United States Patent
Lin

(10) Patent No.: US 10,729,826 B2
(45) Date of Patent: Aug. 4, 2020

(54) WOUND COVER APPARATUS AND RELATED METHODS OF USE

(71) Applicant: Edward D. Lin, Osprey, FL (US)

(72) Inventor: Edward D. Lin, Osprey, FL (US)

( * ) Notice: Subject to any disclaimer, the term of this patent is extended or adjusted under 35 U.S.C. 154(b) by 80 days.

(21) Appl. No.: 15/663,713

(22) Filed: Jul. 29, 2017

(65) Prior Publication Data

US 2019/0030224 A1    Jan. 31, 2019

(51) Int. Cl.
*A61M 1/00* (2006.01)
*A61M 35/00* (2006.01)
(Continued)

(52) U.S. Cl.
CPC ..... *A61M 1/0084* (2013.01); *A61F 13/00068* (2013.01); *A61F 13/0206* (2013.01); *A61F 13/0216* (2013.01); *A61L 15/26* (2013.01); *A61L 15/58* (2013.01); *A61M 1/0037* (2013.01); *A61M 1/0088* (2013.01); *A61M 35/30* (2019.05); *A61F 2013/0017* (2013.01); *A61M 1/0052* (2014.02); *A61M 1/0092* (2014.02);
(Continued)

(58) Field of Classification Search
CPC .............. A61M 1/0084; A61M 1/0092; A61M 1/0088; A61M 2205/75; A61M 2205/50; A61M 2205/3344; A61M 2202/0208; A61M 2205/3337; A61M 1/0037; A61M 1/0052; A61M 35/00; A61F 13/0216; A61F 13/0206; A61F 13/00068; A61F 2013/0017; A61N 2/002; A61L 15/26; A61L 15/58
See application file for complete search history.

(56) References Cited

U.S. PATENT DOCUMENTS 2,280,915 A    4/1942  Johnson
3,026,874 A    3/1962  Stevens
(Continued)

FOREIGN PATENT DOCUMENTS

CH    201010139947.2    1/2016
CN       102008373 A     4/2011
(Continued)

OTHER PUBLICATIONS

International Search Report for International Application No. PCT/US2018/043953 dated Oct. 9, 2018.
(Continued)

*Primary Examiner* — Christine H Matthews
*Assistant Examiner* — Joshua Daryl D Lannu
(74) *Attorney, Agent, or Firm* — Cardle Patent Law Chtd

(57) ABSTRACT

A wound therapy apparatus is disclosed that includes a wound interface securable to a skin surface around a wound bed to form an enclosed space over the wound bed that is fluid-tight. The wound therapy apparatus may include a dressing engaged with the wound interface to contact the wound bed. Gas within the enclosed space may have an $O_2$ concentration greater than the $O_2$ concentration in atmospheric air. The dressing may include a hydrophobic material, hydrophobic material, or a distal layer comprised of silicone having fenestrations therein, in various aspects. The pressure $p_0$ within the enclosed space may vary over a pressure range $p_{min} \leq p_0 \leq p_{max}$. Related methods of use are also disclosed.

20 Claims, 14 Drawing Sheets

(51) Int. Cl.
  *A61F 13/02* (2006.01)
  *A61N 2/00* (2006.01)
  *A61L 15/26* (2006.01)
  *A61L 15/58* (2006.01)
  *A61F 13/00* (2006.01)

(52) U.S. Cl.
  CPC .............. *A61M 2202/0208* (2013.01); *A61M 2205/3337* (2013.01); *A61M 2205/3344* (2013.01); *A61M 2205/50* (2013.01); *A61M 2205/75* (2013.01); *A61N 2/002* (2013.01)

(56) References Cited

U.S. PATENT DOCUMENTS

| | | | |
|---|---|---|---|
| 3,300,786 A | 1/1967 | Rosenvold et al. | |
| 4,163,822 A | 8/1979 | Walter | |
| 4,328,799 A | 5/1982 | LoPiano | |
| 4,399,816 A | 8/1983 | Spangler | |
| 4,635,618 A | 1/1987 | Munz | |
| 5,086,763 A | 2/1992 | Hathman | |
| 5,154,697 A | 10/1992 | Loori | |
| D364,679 S | 11/1995 | Heaton et al. | |
| 5,522,794 A | 6/1996 | Ewall | |
| 5,562,107 A | 10/1996 | Lavender | |
| 5,607,388 A | 3/1997 | Ewall | |
| 5,636,643 A | 6/1997 | Argenta et al. | |
| 5,667,502 A | 9/1997 | Holtermann | |
| 5,769,806 A | 6/1998 | Radow | |
| 5,792,090 A | 8/1998 | Ladin | |
| 5,899,207 A | 5/1999 | Scheinberg | |
| 5,980,497 A | 11/1999 | Yavitz | |
| 6,062,215 A | 5/2000 | Leininger et al. | |
| 6,098,628 A | 8/2000 | Funk | |
| 6,142,982 A | 11/2000 | Hunt et al. | |
| 6,222,090 B1 | 4/2001 | Weston | |
| 6,328,709 B1 | 12/2001 | Hung et al. | |
| 6,458,109 B1 * | 10/2002 | Henley ............... A61M 1/0088 604/304 |
| 6,484,716 B1 | 11/2002 | Leininger et al. | |
| D469,175 S | 1/2003 | Hall et al. | |
| 6,553,998 B2 | 4/2003 | Heaton et al. | |
| D475,134 S | 5/2003 | Randolph | |
| 6,695,823 B1 | 2/2004 | Lina et al. | |
| D488,588 S | 4/2004 | Hall | |
| 6,764,462 B2 | 7/2004 | Risk et al. | |
| 6,767,334 B1 | 7/2004 | Randolph | |
| 6,767,344 B2 | 7/2004 | Suzuki | |
| 6,814,079 B2 | 11/2004 | Heaton et al. | |
| 6,824,533 B2 | 11/2004 | Risk, Jr. et al. | |
| 6,856,821 B2 | 2/2005 | Johnson | |
| 6,936,037 B2 | 8/2005 | Bubb et al. | |
| 6,951,553 B2 | 10/2005 | Bubb et al. | |
| 7,108,683 B2 | 9/2006 | Zamierowski | |
| 7,154,017 B2 | 12/2006 | Sigurjonsson et al. | |
| 7,532,953 B2 | 5/2009 | Vogel | |
| 7,534,240 B1 | 5/2009 | Johnson | |
| 7,608,066 B2 | 10/2009 | Vogel | |
| 7,790,945 B1 | 9/2010 | Watson, Jr. | |
| 7,837,673 B2 | 11/2010 | Vogel | |
| 7,909,805 B2 | 3/2011 | Weston | |
| 7,964,766 B2 | 6/2011 | Blott et al. | |
| D642,594 S | 8/2011 | Mattson et al. | |
| D648,353 S | 11/2011 | Mattson et al. | |
| 8,080,702 B2 | 12/2011 | Blott et al. | |
| 8,142,405 B2 | 3/2012 | Vogel | |
| 8,187,237 B2 | 5/2012 | Seegert | |
| 8,529,532 B2 | 9/2013 | Pinto et al. | |
| 8,563,604 B2 | 10/2013 | Palefsky et al. | |
| 8,708,982 B2 | 4/2014 | Lin | |
| 8,821,419 B1 | 9/2014 | Beek | |
| 9,913,757 B2 | 3/2018 | Vitaris | |
| 9,925,361 B2 | 3/2018 | Lin | |
| 2001/0029956 A1 | 10/2001 | Argenta | |
| 2001/0041188 A1 | 11/2001 | Gibbins et al. | |
| 2002/0017304 A1 | 2/2002 | Heaton et al. | |
| 2002/0143286 A1 | 10/2002 | Tumey | |
| 2002/0155164 A1 | 10/2002 | Figley | |
| 2003/0014022 A1 | 1/2003 | Lockwood | |
| 2003/0021775 A1 | 1/2003 | Freeman | |
| 2003/0040687 A1 | 2/2003 | Boynton et al. | |
| 2003/0050594 A1 | 3/2003 | Zamierowski | |
| 2003/0212357 A1 | 11/2003 | Pace | |
| 2003/0219469 A1 | 11/2003 | Johnson et al. | |
| 2004/0006319 A1 | 1/2004 | Lina et al. | |
| 2004/0010207 A1 | 1/2004 | Flaherty | |
| 2004/0073151 A1 | 4/2004 | Weston | |
| 2004/0093026 A1 | 5/2004 | Weidenhagen et al. | |
| 2004/0153032 A1 | 8/2004 | Garribotto et al. | |
| 2004/0170703 A1 | 9/2004 | Hoekstra et al. | |
| 2005/0137521 A1 | 6/2005 | Stenzler | |
| 2005/0220849 A1 | 10/2005 | Hickey | |
| 2005/0228340 A1 | 10/2005 | Cleary | |
| 2006/0127462 A1 | 6/2006 | Canada et al. | |
| 2006/0146234 A1 | 7/2006 | Bear et al. | |
| 2006/0185670 A1 | 8/2006 | Loori et al. | |
| 2007/0041960 A1 | 2/2007 | Freeman et al. | |
| 2007/0118096 A1 | 5/2007 | Smith | |
| 2008/0140029 A1 | 6/2008 | Smith et al. | |
| 2009/0258058 A1 | 10/2009 | Thomas et al. | |
| 2009/0312723 A1 | 12/2009 | Blott et al. | |
| 2010/0268128 A1 | 10/2010 | Randolph | |
| 2010/0298792 A1 | 11/2010 | Weston et al. | |
| 2011/0160686 A1 * | 6/2011 | Ueda ............... A61F 13/0203 604/365 |
| 2012/0029449 A1 | 2/2012 | Khosrowshahi | |
| 2013/0053795 A1 | 2/2013 | Coulthard et al. | |
| 2013/0053806 A1 | 2/2013 | Guillo et al. | |
| 2013/0165837 A1 | 6/2013 | Addison et al. | |
| 2013/0211318 A1 | 8/2013 | Croizat et al. | |
| 2013/0231623 A1 | 9/2013 | Richard | |
| 2013/0303975 A1 | 11/2013 | Gvodas, Jr. | |
| 2014/0081192 A1 | 3/2014 | Wenske et al. | |
| 2014/0114268 A1 | 4/2014 | Auguste et al. | |
| 2014/0155790 A1 | 6/2014 | Argenta et al. | |
| 2014/0207027 A1 | 7/2014 | Navia et al. | |
| 2014/0309574 A1 | 10/2014 | Cotton | |
| 2015/0005678 A1 | 1/2015 | Wall | |
| 2015/0088085 A1 | 3/2015 | Rovaniemi | |
| 2015/0119832 A1 | 4/2015 | Locke | |
| 2016/0000610 A1 | 1/2016 | Riesinger | |
| 2016/0074232 A1 | 3/2016 | Vitaris et al. | |
| 2016/0128894 A1 | 5/2016 | Horton et al. | |
| 2016/0166781 A1 | 6/2016 | Sarangapani et al. | |
| 2016/0256665 A1 | 9/2016 | Doshi et al. | |
| 2016/0262944 A1 | 9/2016 | Shmuelovitch et al. | |
| 2017/0119940 A1 | 5/2017 | Quisenberry | |
| 2018/0169395 A1 | 6/2018 | Lin | |
| 2019/0029886 A1 | 1/2019 | Lin | |
| 2019/0030223 A1 | 1/2019 | Lin | |
| 2019/0030224 A1 | 1/2019 | Lin | |
| 2019/0030225 A1 | 1/2019 | Lin | |
| 2019/0030226 A1 | 1/2019 | Lin | |

FOREIGN PATENT DOCUMENTS

| | | |
|---|---|---|
| CN | 101969902 B | 2/2013 |
| CN | 102985096 A | 3/2013 |
| CN | 104024498 A | 9/2014 |
| CN | 106659590 A | 5/2017 |
| EP | 0206646 | 12/1986 |
| EP | 0940131 | 9/1999 |
| EP | 0940131 A2 | 9/1999 |
| EP | 1219311 | 7/2004 |
| EP | 1018967 | 8/2004 |
| EP | 1674898 | 6/2006 |
| EP | 1901686 | 7/2014 |
| EP | 2995324 A1 | 3/2016 |
| EP | 3156016 | 4/2017 |
| GB | 288220 | 8/1928 |
| GB | 2265314 | 9/1993 |
| GB | 2329127 | 3/1999 |
| GB | 2351025 | 12/2000 |
| GB | 2365350 | 2/2002 |
| GB | 2496310 B | 10/2015 |

(56) References Cited

FOREIGN PATENT DOCUMENTS

| WO | 9605873 | | 2/1996 | | |
|---|---|---|---|---|---|
| WO | 0059418 | | 10/2000 | | |
| WO | 0059424 | | 10/2000 | | |
| WO | 03049660 | | 6/2003 | | |
| WO | 2003092620 | | 11/2003 | | |
| WO | 2004060148 | | 7/2004 | | |
| WO | 2005009488 | | 2/2005 | | |
| WO | 2005046761 | A1 | 5/2005 | | |
| WO | 2006081403 | A1 | 8/2006 | | |
| WO | WO-2009141820 | A1 * | 11/2009 | ......... | A61M 1/0084 |
| WO | 2011130246 | A2 | 10/2011 | | |
| WO | 2013066694 | A2 | 5/2013 | | |
| WO | 2013123005 | A1 | 8/2013 | | |
| WO | 2015193257 | A1 | 12/2015 | | |
| WO | 2019027806 | A1 | 2/2019 | | |
| WO | 2019027807 | A1 | 2/2019 | | |
| WO | 2019027808 | A1 | 2/2019 | | |
| WO | 2019027809 | A1 | 2/2019 | | |
| WO | 2019027810 | A1 | 2/2019 | | |

OTHER PUBLICATIONS

International Search Report for International Application No. PCT/US2018/043955 dated Oct. 17, 2018.
International Search Report for International Application No. PCT/US2018/043957 dated Oct. 19, 2018.
International Search Report for International Application No. PCT/US2018/043959 dated Oct. 15, 2018.
International Search Report for International Application No. PCT/US2018/043962 dated Oct. 16, 2018.
Cardinal Health NPWT Pro Family, Cardinal Health, Waukegan, IL, 2015.
Cardinal Health SVED Clinician User Manual, Cardinal Health, Waukegan, IL, 2015.
Cardinal Health SVED Wound Care Anywhere, Cardinal Health, Waukegan, IL, 2015.
Cardinal Health SVED Clinician Quick Reference Guide, Cardinal Health, Waukegan, IL, 2015.
Cardinal Health SVED Patient User Manual, Cardinal Health, Waukegan, IL, 2015.
ITI Brings Hospitals New Value Model for Wound Care, Innovative Therapies, Inc. Copyright 2013 PR Newswire.
Application Guide: Pico multisite with softport technology applied to the heel, PCPE-48/0717-UE, Smith & Nephew, Inc. 2017.
Avance® Clinician's Guidelines, Revision Feb. 2017, Mölnlycke Health Care US, LLC, Norcross, GA 30092.
Borgquist, O., R. Ingemansson, M Malmsjö, Effects of negative pressure wound therapy on regional blood flow, wound contraction and fluid removal—Examining low pressure levels, intermittent and variable therapy, 24th Annual Clinical Symposium on Advances in Skin & Wound Care, San Antonio, Texas, USA—Oct. 22-25, 2009.

Borgquist, Ola, et al. Wound Edge Microvascular Blood Flow during Negative-Pressure Woulnd Therapy: Examining the Effects of Pressures from -10 to -175 mmHg, PRSJournal, vol. 125, No. 2, 2010, 502-509.
Chanden K. Sen, Wound healing essentials: Let there be oxygen, Wound Rep Reg (2009) 17 1-18.
Eriksson, et al., Wet wound healing: from laboratory to patients to gene therapy, The American Journal of Surgery 188 (Suppl to Jul. 2004) 36S-41S.
EZCare Negative Pressure Wound Therapy, V1STA Negative Pressure Wound Therapy, Negative Pressure Wound Therapy Clinical Guidelines, BS-0039-0808, Smith & Nephew.
Final Rejection, U.S. Appl. No. 15/663,710, dated Nov. 25, 2019.
Ghatak, Schlanger, Ganesh, Lambert, Gordillo, Martinsek,and Roy, A Wireless Electroceutical Dressing Lowers Cost of Negative Pressure Wound Therapy, Adv Wound Care (New Rochelle) 4(5): 302-311, May 2015.
Malsmjo, MD, et al, Negative pressure wound therapy using gauze or polyurethane open cell foam: similar effects on would edge microvascular blood flow, Lund University, 1 page.
Niederauer, Mark Q. et al. Continuous diffusion of oxygen improves diabetic foot ulcer healing when compared with a placebo control: a randomised, double-blind, multicentre study, J. Wound Care, N. American Supplement, vol. 27, No. 9, Sep. 2018.
Non Final Rejection, U.S. Appl. No. 15/663,710, dated Jul. 11, 2019.
Non-Final Office Action, U.S. Appl. No. 15/663,708, dated Nov. 7, 2019.
Non-Final Rejection, U.S. Appl. No. 15/663,709, dated Oct. 10, 2019.
Non-Final Rejection, U.S. Appl. No. 15/663,714, dated Sep. 13, 2019.
Notice of References Cited, U.S. Appl. No. 15/663,708.
Notice of References Cited, U.S. Appl. No. 15/663,709.
Notice of References Cited, U.S. Appl. No. 15/663,710.
Notice of References Cited, U.S. Appl. No. 15/663,714.
Prevena Incision Management System, Clinician Guide, 390061 Rev C, KCI Licensing Inc., 2009.
Prevena Incision Management System, Product Monograph, KCI Licensing Inc., 2010.
Prospera Negaitve Pressure Wound Therapy, Pro-I, Advancing the Art and Science of NPWT, Prospera, Ft. Worth, TX, 2008. MR-125-04/08.
Renasys Negative Pressure Wound Therapy, Pico Single Use Negative Pressure Wound Therapy System, NIPCE-48-0613-NAE, Smith & Nephew, Inc., 2013.
V.A.C. Ulta Quick Reference Guide, KCI Licensing Inc., 2013.
V.A.C.Ulta™ Negative Pressure Wound Therapy System, KCI Licensing Inc., Apr. 17, 2016.
Final Rejection, U.S. Appl. No. 15/663,714 dated Feb. 3, 2020.

* cited by examiner

WOUND COVER APPARATUS AND RELATED METHODS OF USE

CROSS-REFERENCE TO RELATED APPLICATIONS

This application hereby incorporates by reference in the entirety herein the co-pending U.S. patent application Ser. No. 15/663,708 entitled "DEFORMATION RESISTANT WOUND THERAPY APPARATUS AND RELATED METHODS OF USE," co-pending U.S. patent application Ser. No. 15/663,709 entitled "AUGMENTED PRESSURE THERAPY FOR WOUNDS," co-pending U.S. patent application Ser. No. 15/663,710 entitled "CONTROL APPARATUS AND RELATED METHODS FOR WOUND THERAPY DELIVERY," co-pending U.S. patent application Ser. No. 15/663,714 entitled "WOUND THERAPY APPARATUS WITH SCAR MODULATION PROPERTIES AND RELATED METHODS," all by Edward D. Lin as inventor and applicant and filed on 29 Jul. 2017.

BACKGROUND OF THE INVENTION

Field

This invention relates to medical devices, and more particularly, to wound therapy apparatus and related compositions of matter and methods of use.

Related Art

Wounds afflict hundreds of millions of people globally. In the US, 6.5 million chronic wounds exist with average healing time of 23 weeks due principally to inadequate blood flow and insufficient oxygen. There are 71 million acute surgical wounds with a growing incidence of surgical site infections. Many types of bandages and dressings have been created to improve various aspects of healing. However, a majority of these various bandages and dressings offer narrow benefits focused on only a particular aspect of the multifaceted needs of healing of a wound bed such as maintaining moisture and preserving sterility. For example, dressing impregnated with silver inhibits infection due to antimicrobial properties, but silver also inhibits fibroblast differentiation and healing. Hydrocolloids may absorb exudate from the wound bed but do nothing to improve blood flow and oxygenation. Silicone dressings may help to reduce scar formation but silicone dressings lack absorbent properties and may be a barrier to exudate transfer.

A silicone sheet applied over a wound bed has been shown to reduce scar formation. The silicone sheet is typically applied to a wound bed that has healed to induce collagen reconfiguration, resulting in a less prominent scar. The silicone sheet is a barrier to exudate transfer, and therefore by conventional wisdom is not suitable for use during the exudative phase of healing of the wound bed.

Absorbent bandages, for example Pico by Smith & Nephew and Prevena™ by Acelity, that provide NPWT (negative pressure wound therapy) suction to the wound bed were introduced in the US in the early 2010's. The negative pressure in these devices is produced by a single-use battery-powered pump that applies a constant suction to the wound. After 7 days of use, the pump is 'killed' (permanently deactivated) by software and the dressing and pump are both discarded. Although helping to remove exudate, the constant suction may collapse certain capillaries and decrease blood flow as well as tissue oxygen tension in certain regions, both of which may be unconducive to healing. This is a frequent condition when NPWT is used to treat acute and chronic wounds.

Accordingly, there is a need for improved apparatus as well as related methods for wound therapy that may, for example, offer comprehensive benefits and address various wound healing challenges.

BRIEF SUMMARY OF THE INVENTION

These and other needs and disadvantages may be overcome by the apparatus and related methods of use and compositions of matter disclosed herein. Additional improvements and advantages may be recognized by those of ordinary skill in the art upon study of the present disclosure.

In various aspects, a wound therapy apparatus is disclosed herein that includes a wound interface securable to a skin surface around a wound bed to form an enclosed space over the wound bed that is fluid-tight in order to maintain a pressure $p_0$ within the enclosed space that differs from the ambient pressure $p_{amb}$. The wound therapy apparatus, in various aspects, includes a dressing engaged with the wound interface to contact the wound bed. An adhesive layer may be formed on distal surfaces of the wound interface to secure the wound interface to the skin surface. When secured to the skin surface, the wound therapy apparatus includes gas within the enclosed space having an $O_2$ concentration greater than the $O_2$ concentration in atmospheric air, there being no gas flow into the enclosed space or out of the enclosed space, in various aspects.

The dressing may include a hydrophobic material that transfers exudate from the wound bed, and a hydrophilic material in fluid cooperation with the hydrophobic material to transfer exudate from the hydrophobic material, in various aspects. The dressing includes at least a distal layer comprised, at least in part, of silicone, a distal side of the distal layer contacts the wound bed when the wound interface is secured to the skin, and fenestrations are disposed in the distal layer that fluidly communicate between the distal side and a proximal side of the distal layer, in various aspects.

Related methods of use may include the step of inputting input fluid may into the enclosed space or withdrawing output fluid from the enclosed space through one or more lumen to vary the pressure $p_0$ within the enclosed space over a pressure range $p_{min} \leq p_0 \leq p_{max}$. In certain aspects, the maximum pressure $p_{max}$ may be greater than ambient pressure $p_{amb}$. In certain aspects, the input fluid may be a gas that may have an $O_2$ concentration greater than the $O_2$ concentration in atmospheric air. In certain aspects, the input fluid may be a liquid, and the liquid may be sequentially input into the enclosed space and then withdrawn from the enclosed space or the liquid may be simultaneously input into the enclosed space and withdrawn from the enclosed space, in various aspects.

This summary is presented to provide a basic understanding of some aspects of the apparatus and methods disclosed herein as a prelude to the detailed description that follows below. Accordingly, this summary is not intended to identify key elements of the apparatus, methods, and compositions of matter disclosed herein or to delineate the scope thereof.

Figure 1A:
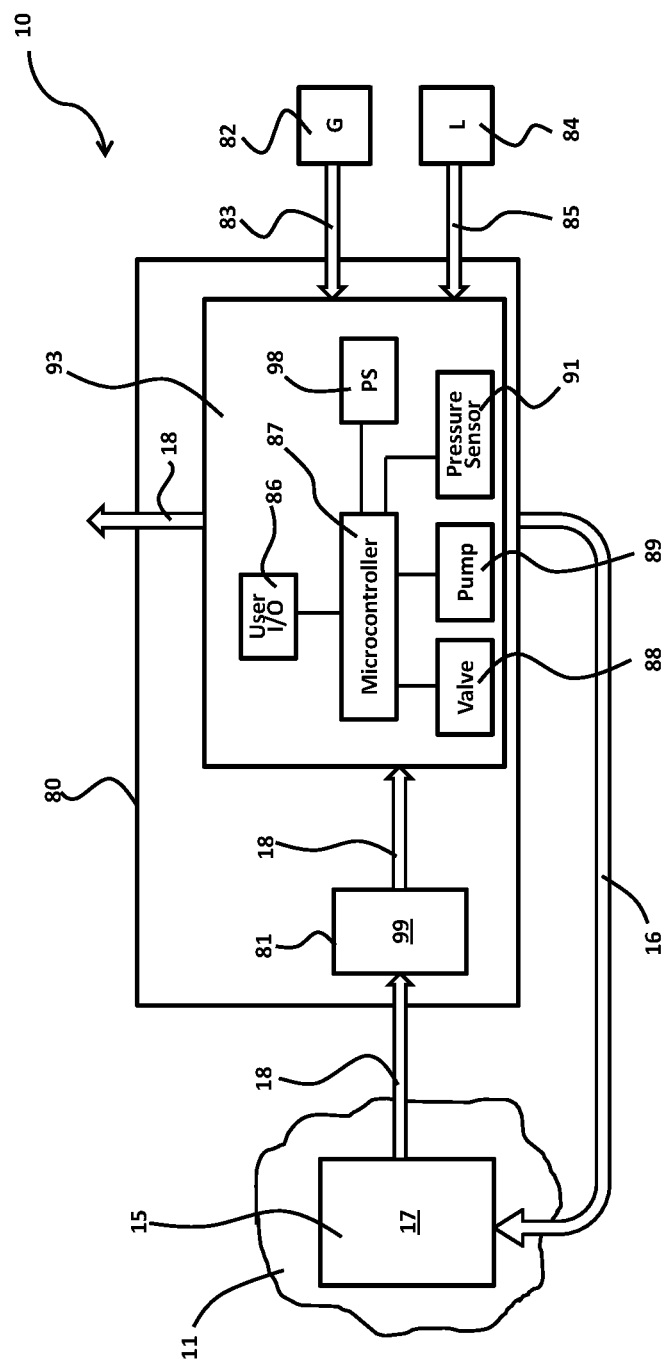
FIG. 1A illustrates by schematic view an exemplary implementation of a wound therapy apparatus.

The Figures are exemplary only, and the implementations illustrated therein are selected to facilitate explanation. The number, position, relationship and dimensions of the elements shown in the Figures to form the various implementations described herein, as well as dimensions and dimensional proportions to conform to specific force, weight, strength, flow and similar requirements are explained herein or are understandable to a person of ordinary skill in the art upon study of this disclosure. Where used in the various Figures, the same numerals designate the same or similar elements. Furthermore, when the terms "top," "bottom," "right," "left," "forward," "rear," "first," "second," "inside," "outside," and similar terms are used, the terms should be understood in reference to the orientation of the implementations shown in the drawings and are utilized to facilitate description thereof. Use herein of relative terms such as generally, about, approximately, essentially, may be indicative of engineering, manufacturing, or scientific tolerances such as ±0.1%, ±1%, ±2.5%, ±5%, or other such tolerances, as would be recognized by those of ordinary skill in the art upon study of this disclosure.

DETAILED DESCRIPTION OF THE INVENTION

A wound therapy apparatus is disclosed herein. In various aspects, the wound therapy apparatus includes a wound interface securable to a skin surface around a wound bed to form an enclosed space over the wound bed that sufficiently fluid-tight to maintain a pressure $p_0$ within the enclosed space that is either greater than or less than the ambient pressure $p_{amb}$. A gas may be provided within the enclosed space having an $O_2$ concentration greater than atmospheric air, or greater than about 20.95% oxygen by volume for dry atmospheric air or 0.2095 mole $O_2$ per mole of atmospheric air, in various aspects. The wound therapy apparatus may include a dressing disposed within the enclosed space to bias against the wound bed, and the dressing may include at least a distal layer and a proximal layer of differing compositions. The wound interface may include an adhesive layer to adhesively secure the wound interface to the skin surface around the wound bed.

Wound bed, as used herein, means a focal breach in the external surface of normal skin, for example, from trauma (such as abrasion, avulsion, tearing, piercing, cutting, chemical or thermal injury) or microbial infection. The wound bed may include varying degrees of exposure of underlying layers and structures, along with possible infections and tissue changes. The wound bed represents an unhealed wound. In contrast, a healed wound is a skin surface that was previously injured but the focal breach is now entirely sealed and covered by varying amounts of epidermis and scar tissue.

Silicone, as used herein, includes siloxane, various polysiloxanes, silicone-like materials, and various combinations thereof that may be generally solid. Silicone may have the chemical formula $[R_2SiO]_n$, where R is an organic group. Silicone may include, for example, silicone polymers having an average molecular weight in excess of 100,000 (e.g., between about 100,000 and about 10,000,000). Examples may include, but are not limited to, crosslinked siloxanes (e.g., crosslinked dimethicone or dimethicone derivatives), copolymers such as stearyl methyl-dimethyl siloxane copolymer, polysilicone-11 (a crosslinked silicone rubber formed by the reaction of vinyl terminated silicone and (methylhydro dimethyl)polysiloxane in the presence of cyclomethicone), cetearyl dimethicone/vinyl dimethicone crosspolymer (a copolymer of cetearyl dimethicone crosslinked with vinyl dimethyl polysiloxane), dimethicone/phenyl vinyl dimethicone crosspolymer (a copolymer of dimethylpolysiloxane crosslinked with phenyl vinyl dimethylsiloxane), and dimethicone/vinyl dimethicone crosspolymer (a copolymer of dimethylpolysiloxane crosslinked with vinyl dimethylsiloxane).

In various aspects, the gas within the enclosed space having an $O_2$ concentration greater than atmospheric air may be medical grade oxygen. Medical grade oxygen may conform to certain standards, for example, United States Food and Drug Administration standards or other appropriate regulatory standards. In various aspects, the medical grade oxygen may be United States Pharmacopoeia grade oxygen.

The wound therapy apparatus may include one or more ports with one or more lumen that fluidly communicate with the enclosed space to periodically vary the pressure $p_0$ within the enclosed space over a pressure range $p_{min} \leq p_0 \leq p_{max}$ by flowing fluid into or out of the enclosed space through the one or more ports. The wound therapy apparatus may include various fluid conveyances or sources of fluid as may be operably coupled with the wound interface to input fluid into the enclosed space or withdraw fluid from the enclosed space. In various aspects, fluid may be input into the enclosed space sequentially with withdrawal of fluid from the enclosed space so that fluid is not input into the enclosed space simultaneously with withdrawal of fluid from the enclosed space.

In certain aspects when flowing liquid through the enclosed space, it may be desirable to input liquid into the enclosed space while simultaneously withdrawing the liquid from the enclosed space. In certain aspects the passage of liquid through the enclosed space may be limited in duration, for example, to a duration of 30-90 minutes in order to prevent (1) local hypothermia and vasoconstriction to the wound and (2) tissue maceration to the peri-wound skin. Such undesirable side effects may in turn be prevented by (1) pre-warming the liquid and (2) applying a layer of cyanoacrylate-like adhesive to the peri-wound skin before therapy to protect the skin from prolonged contact with liquids.

Sequential input of input fluid into the enclosed space (at the end of an NPWT cycle) and withdrawal of output fluid from the enclosed space (at the start of the next NPWT cycle) means that the input of input fluid and withdrawal of output fluid does not occur simultaneously, with the exception of flowing liquid through the enclosed space. Other than this exception, input fluid may be being input into the enclosed space or output fluid may be being withdrawn from the enclosed space but not the input of input fluid simultaneously with withdrawal of output fluid when input of input fluid and withdrawal of output fluid are sequential.

Fluid, as used herein, includes, liquid(s), gas(ses), and combinations thereof. Liquid may include, for example, Dakins' solution, saline solution, antioxidant solution, proteolytic enzyme solutions, antimicrobial solutions, amniotic fluid, and exudate. Liquid may include solutions for irrigating the wound bed, removal of bio-burden, or moisturizing the wound bed. Gas may include, for example, atmospheric air, oxygen, nitric oxide, nitrogen, humidity, or suitable therapeutic or inert gasses, and combinations thereof. Humidity, as used herein, includes water vapor and mist. Exudate, as used herein, includes, for example, proteinaceous liquids exuded from the wound bed, along with various plasma and blood components. Exudate may also include other liquids including other liquids exuded by the wound bed.

In various aspects, the term fluid-tight or related terms, as used herein, means sufficiently leak-resistant to allow insufflation or vacuum suction to create pressure $p_0$ within the enclosed space that may be above or below ambient pressure $p_{amb}$. The term fluid-tight means sufficiently leak-resistant to substantially retain fluids including both gasses and liquids within the enclosed space other than by controlled fluid communication through one or more lumen that fluidly communicate through the wound interface with the enclosed space, in certain aspects. In certain aspects, fluid-tight means sufficiently leak-resistant to maintain pressure $p_0$ within the enclosed space above or below ambient pressure $p_{amb}$.

Ambient pressure $p_{amb}$, as used herein, refers to the pressure in a region surrounding the wound therapy apparatus. Ambient pressure $p_{amb}$, for example, may refer to atmospheric pressure, hull pressure within an aircraft where the wound therapy apparatus is being utilized, or pressure maintained generally within a building or other structure where the wound therapy apparatus is being utilized. Ambient pressure $p_{amb}$ may vary, for example, with elevation or weather conditions. Pressure $p_{min}$ refers to the minimum pressure achieved within the enclosed space of the wound therapy apparatus, and periodically varying of pressure $p_0$, pressure variation, varying pressure, pressure cycle, and similar term refer to changes of pressure $p_0$ within the enclosed space over time, in various aspects. Pressure $p_{max}$ refers to the maximum pressure achieved within the enclosed space of the wound therapy apparatus.

The minimum pressure $p_{min}$ may be, for example, generally within the range of −40 mm Hg to −150 mm below ambient pressure $p_{amb}$. The maximum pressure $p_{max}$ may be, for example, generally within the range of the +5 mm Hg to +40 mm Hg above ambient pressure $p_{amb}$, in some aspects. In certain aspects, the maximum pressure $p_{max}$ may be approximately equal to the ambient pressure $p_{amb}$. In certain aspects, the maximum pressure $p_{max}$ may be generally within the range of −5 mm Hg to −20 mm Hg below ambient pressure $p_{amb}$. The minimum pressure $p_{min}$, maximum pressure $p_{max}$, time period of a pressure cycle, and shape of the pressure cycle (e.g., sinusoidal, square wave) may vary during use of the wound therapy apparatus. In various aspects, the pressure $p_0$ in the enclosed space may be above or below ambient pressure $p_{amb}$ and at a condition of stasis for some period of time. The wound therapy apparatus may provide suction ($p_o < p_{amb}$) that is intermittent including cyclical in nature to enable capillary refill and reperfusion when suction is reduced or off (po→pamb). In certain implementations, the pressure cycles may vary from one another depending on the particular therapy being delivered and the desired effect to be achieved. For example, a saline rinse may be given every 2 hrs for two minutes, an antibiotic infusion may be delivered every 8-12 hrs for a 5-10-minute soak, whereas an infusion of local anesthetic may be needed every 4-12 hrs for only 2-4 minutes depending on the drug used. In various implementations, the suction is relieved by fluid having an $O_2$ concentration greater than atmospheric air, air, or air in combination with $O_2$ to enhance blood flow and oxygenation. In other situations, the suction is relieved by liquid.

The material(s) that form a dressing, in various aspects, may include, for example, foam formulations made of polyvinyl alcohol, polyurethane, especially of the open cell type, polyurethane foam with polyethylene glycol (PEG) to enhance its water absorption and transport characteristics, or other suitable polymers, fibers such as sodium carboxymethyl cellulose hydrofiber (Aquacel) that may be woven, non-woven, or combinations of woven and non-woven. The material(s) that form the dressing, in various aspects, may include, for example, nonwoven fabric comprised of multi-component fibers of nylon and polyester that have been longitudinally split into their individual components by hydroentanglement (Evolon®). The material(s) that form the dressing, in various aspects, may include, for example knitted fibers, such as in the jersey-knit pattern with hydrophobic fibers predominant on the side closest to the wound and hydrophilic fibers predominantly on the side away from the wound in order to serve as a conduit to fluid transfer.

The material(s) that form dressing may be organized in layers with the layers being, for example, of differing compositions (e.g., varying proportions of polypropylene and nylon from one side of a layer to the other, varying concentration or density of a single additive material such as silicone thread from one side to the other, open cell polyvinyl alcohol and cellulose) or differing configurations of the same material (e.g., woven and non-woven), and the dressing may include two or more layers. In certain aspects, the distal layer that is most distal and contacts the wound bed may be formed of silicone that is perforated to allow fluid to pass between a distal side and a proximal side of the distal layer. Or the distal layer may comprise a layer of woven silicone threads of certain mesh to allow such passage while imparting other desirable characteristics such as scar modulation or homogenization of tissue tension across an incisional surface. In certain aspects, a distal layer or surface may be formed predominantly of hydrophobic material(s) and the layer or surface of the dressing that is relatively proximal to the wound bed may be formed of hydrophilic material. The hydrophobic material may communicate liquid, such as exudate, away from the wound bed to prevent liquid buildup and, thus, maceration of tissue with which the dressing is in contact including the skin surface surrounding the wound bed. The hydrophilic material may communicate liquid away from the hydrophobic material, for example, towards the lumen for withdrawal from the enclosed space. The hydrophobic material may be, for example, a polyester-like material, and the hydrophilic material may be, for example, an aliphatic or semi-aromatic polyamid (e.g. Nylon). The dressing may include polyester-polyurethane copolymer fiber (e.g. Spandex or Lycra) for stretchability and conformability, and to apply a gentle compressive force to the wound bed. Polyurethane foam with polyethylene glycol (PEG) added may enhance absorption and exudate transport. And since PEG may expand multifold (7× to 12× or more, depending on composition) and yet only exert gentle pressure, it may be useful in providing gentle compression without perfusion compromise in skin grafting. Such gentle compressive force exerted by the dressing on the wound bed may reduce underlying edema, and in the case of surgical incision wounds, may help appose the two wound edges and reduce seroma formation in between. In some implementations, distal side of the dressing in contact with the wound bed may be formed of material known to separate easily from wound during dressing changes and minimize pain, discomfort and disruption to granulation tissue. Examples include a silicone sheet with fenestrations, silicone threads weaved in with a suitable mesh or other perforated nonstick polymer films such as polyethylene terephthalate (PET) polytetrafluoroethylene (PTFE), or other fluoropolymers.

The dressing may include medicament(s), the medicament(s) may be pre-loaded onto the dressing, and the medicament(s) may be delivered to the wound bed when the wound interface is secured to the skin surface. In certain aspects, the medicament(s) may be supplied to the dressing when the wound interface including the dressing is secured to the skin surface. It is also envisioned that certain drug delivery pods may be functionally coupled with the dressing and supplied to the dressing just prior to use by, for example, a prefilled delivery unit such as prefilled syringes, crushable ampoules, or puncture-and-squeeze delivery devices. Medicament may include, for example, silver ion releasing formulations or antibiotic for antimicrobial activity, analgesic for pain reduction, antioxidants, amniotic or placental derived cytokines and growth factors, platelet rich plasma, hemostatics and coagulants to stop bleeding, oxygen generating and releasing compounds, or exo-or endothermic reagents.

As used herein the terms distal and proximal are relative, not necessarily absolute positional terms defined from the point of view of a physician, including nurses, technicians, and other caregivers, treating a patient with the wound therapy apparatus. A distal portion of the wound therapy apparatus may be oriented toward the patient while a proximal portion of the wound therapy apparatus may be oriented toward the physician. When deployed, for example, a distal portion of the wound therapy apparatus may be closer to the patient while a proximal portion of the wound therapy apparatus may be closer to the physician. As a further example, a distal surface in a multi-layer wound interface is closer to the wound bed, but not necessarily the layer in contact with or closest to the wound bed.

In various aspects, the wound therapy apparatus may include a distal layer of absorbent material applied over a wound, a proximal layer of (generally) impermeable material covering the distal layer of material and sealing the distal layer against the exterior environment in a fluid-tight manner, and at least one port disposed atop the proximal layer that is in functional connection with the absorbent material, and wherein the port is in functional connection with a suction source and a fluid source such as oxygen source.

In various aspects, the wound therapy apparatus may include a distal layer of silicone, including other non-stick polymers such as, for example, polyethylene terephthalate (PET), polytetrafluoroethylene (PTFE), or other fluoropolymers, in contact with a wound bed, the distal layer of silicone has fenestrations within it to allow fluid migration through the layer. A proximal layer of absorbent material may be juxtaposed against a proximal side of the distal layer, the proximal layer being capable of absorbing and wicking exudate away from the distal layer.

In various aspects, the wound therapy apparatus may include a distal layer of absorbent material applied to a wound bed, and a member generally impermeable to fluid except for water vapor, covering the distal layer of material and sealing the distal layer against the exterior environment in a substantially fluid-tight manner. At least one port may be disposed about the member that is in fluid communication with said absorbent material and in fluid communication with a suction source and an oxygen source.

In various aspects, the wound therapy apparatus may include a fluid-conductive material in contact with the wound bed, said fluid-conductive material is also in functional contact with at least one connector and the at least one connector is connectable to a source of controlled suction and oxygen for therapy to the wound. An adhesive proximal layer may secure the absorbent material against the wound and form a fluid-tight seal and enclosed space about the wound.

In various aspects, the fluid-conductive material has structural elements or material composition variances within to facilitate fluid transfer and absorbency away from wound during suction and oxygen delivery to the wound during oxygen therapy, such structural elements include tubing, channels, grooves, tunnels, partitioned layers, interstitial lacunae, spacers, and baffles, at least one portion of which may additionally be interconnected, or varying concentration or proportion of materials from one surface or layer to the other.

A progressive marking or designation system (such as 1, 2, 3 or color coded red to yellow to green) may be employed to indicate the suitability of an implementation of the wound therapy apparatus, for example, for indexing with a corresponding controller setting, to indicate absorbent volume capacity, for a particular stage of wound healing or for a particular type of wound bed. For example, a distal layer formed of silicone with larger fenestrations and thicker absorbent layer may be suitable for use at early stages of the healing process while, very fine fenestrations with thinner absorbent layer may be suitable during later stages of the healing process when less or no exudate is being emitted from the wound bed.

In various aspects, the apparatus and related methods of use and compositions of matter described herein may impart special functionalities to them, including accelerate healing, prevent surgical site infection, harmonize surgical incision surface tension and reduce wound scar formation. For example, chronic wound therapy using current wound therapy devices may be protracted, all 24 hours a day are already fully consigned to round the clock wound therapy for many weeks, if not many months, or even longer. In various aspects, various beneficial therapies may be applied to the wound bed using the wound therapy apparatus and related methods of use disclosed herein without introducing a constant flow of other therapeutics and without reducing the duration of wound therapy. In human terms, this would be as if a person could gain many extra hours a day, in addition to what he is already doing in 24 hours. It is disclosed herein how to achieve additional therapy, for example, by using pressure $p_{min}$ to draw a therapeutic into the enclosed space to begin the additional therapy. The additional therapy, in various aspects, is sandwiched or inserted in the "down" or relief phase of an NPWT cycle. For example, the pressure cycle may have 4 minutes of pressure $p_{min}$ and 2 minutes of relief at pressure $p_{max}$. Using those 2 minutes at pressure $p_{max}$ to deliver oxygen, for example, would result in 8 hours/day of crucially-needed additional oxygen supplementation where previously none existed. Similarly, cycles of saline irrigation, antibiotic or topical anesthetic instillation inserted during relief at pressure $p_{max}$ (between periods of pressure $p_{min}$) may now enable a sustained maintenance of a new, more favorable healing environment, as well as the therapeutic efficacy and patient comfort that previously has been unattainable.

The wound therapy apparatus and related methods of use and compositions of matter disclosed herein combine cyclical NPWT with the healing and infection inhibiting properties of topical oxygen, in various aspects. The wound therapy apparatus disclosed herein provide cyclical NPWT treatment that is relieved by oxygen or other therapeutic fluids to augment the total therapeutic benefit, in various aspects. The wound therapy apparatus disclosed herein provide a dressing having a perforated silicone layer in conjunction with an absorbent layer to produce not only exudate absorbency, but also incision tension harmonization in addition to silicone's scar modulating effect, in various aspects. The wound therapy apparatus and related methods of use deliver other beneficial therapies such as healing cytokines from amniotic fluid, in various aspects. The wound therapy apparatus, in various aspects, may have uses other than wound care, for example, treatment of wrinkles, inflammation, pain, autoimmune processes, pigmented spots, or vitiligo.

FIG. 1A illustrates exemplary wound therapy apparatus 10. As illustrated in FIG. 1A, wound therapy apparatus includes gas source 82 and liquid source 84 in fluid communication with controller 80, and controller 80 is in fluid communication with wound interface 15. Wound interface 15 is secured to skin surface 11 to define enclosed space 17 over wound bed 13 (see FIG. 4A), as illustrated.

Controller 80, in this implementation, includes control group 93 and canister 81 with cavity 99. Canister 81 (which may include filters, and exudate solidifying materials within cavity 99 such as superabsorbent polymers (SAPs) such as sodium polyacrylate) may be detachable from controller 80 for replacement. Canister 81 may be omitted in certain implementations.

Control group 93 includes microcontroller 87 in operative communication with power source 98, user I/O 86, valve 88, pump 89, and pressure sensor 91 to control or monitor the operation of power source 98, valve 88, pump 89, pressure sensor 91, at least in part in response to the user inputs. Microcontroller 87 may include, for example, a microprocessor, memory, A/D converter, D/A converter, clock, I/O connectors, and so forth, as would be readily recognized by those of ordinary skill in the art upon study of this disclosure.

Power source 98 may be, for example, mains electric or battery, and power source 98 may include, for example, a transformer, inverter, rectifier, or power filter. Valve 88 and pressure sensor 91 may be representative of several valves and several pressure sensors, respectively, in this illustration. Various communication pathways may be disposed about controller 80 to communicate electrical power from power source 98 to microcontroller 87, valve 88, pump 89, and pressure sensor 91.

User I/O 86 may include various switches, push buttons, dials, displays, and so forth, whether virtual or physical for obtaining user inputs that are then communicated to microcontroller 87 in order to allow the user to direct the operation of wound therapy apparatus 10. Various communication pathways such as electrical, electromagnetic (e.g. Bluetooth), optical (e.g. LASER, IR), and networked communications may be employed for communication between microcontroller 87 and user I/O 86. User I/O 86 may be located remotely, at least in part, from other components of control group 93, and user I/O 86 may communicate by network including the Internet with other components of control group 93. Microcontroller 87 may control the operation of wound therapy apparatus 10 including controller 80 based, at least in part, upon user inputs communicated to microcontroller 87 from user I/O 86. Microcontroller 87 may communicate data to user I/O indicative of the operation of wound therapy apparatus 10, and user I/O 86 may display this data to the user.

As illustrated in FIG. 1A, gas source 82 fluidly communicates gas 83 with control group 93 of controller 80, and liquid source 84 fluidly communicates liquid 85 with control group 93 of controller 80. Control group 93 of controller 80 as controlled by microcontroller 87 is operable to select neither gas nor liquid input, which in conjunction with pump evacuation would create and maintain a preset negative pressure within enclosed space 17 in wound interface 15. Control group 93 may also select either gas 83 from gas source 82 or liquid 85 from liquid source 84 as input fluid 16 to relieve the negative pressure in a cyclical or intermittent manner. Control group 93 of controller 80 as controlled by microcontroller 87 is operable to control the optional flow of input fluid 16 from controller 80 to enclosed space 17 of wound interface 15, the flow of output fluid 18 from enclosed space 17 of wound interface 15 towards controller 80, and the exhausting of at least portions of output fluid 18 into the canister 81 or atmosphere using valve 88, pump 89, and pressure sensor 91, in this implementation.

In some implementations, for example, the input fluid 16 may include oxygen at a concentration greater than that of atmospheric air, and the output fluid 18 may include exudate and various gass(es), in which case, the exudate may optionally be trapped in one or more layers of absorbent material within the wound interface 15 and not be further transported to canister 81. In some implementations, especially when the input fluid 16 may comprise liquid such as irrigation fluid, the output fluid 18 may be transported to cavity 99 of canister 81.

Valve 88 may include one or more valves disposed about controller 80 and operable, for example, to select input fluid 16 as either gas 83 from gas source 82 or liquid 85 from liquid source 84, to control the flow of input 16 from controller 80 to enclosed space 17 of wound interface 15, and to control the flow of output fluid 18 from enclosed space 17 of wound interface 15 towards controller 80. Pressure sensor 91 may include one or more pressure sensors operable, for example, to monitor pressure at various locations in gas 83, liquid, 85, input fluid 16, output fluid 18, or enclosed space 17 of wound interface 15. Microcontroller 87 may alter the operation of valve 88 in response to signals from pressure sensor 91. Input fluid 16 may be communicated under pressure at gas source 82 or liquid source 84, and pump 89 may be used to withdraw output fluid 18 from enclosed space 17 towards canister 81. While pressure $p_0$ in the enclosed space 17 is being maintained at either $p_{max}$ or at $p_{min}$, there may be no input of input fluid 16 into the enclosed space 17. With pressure $p_0$ in the enclosed space 17 at $p_{min}$, input fluid 16 from either gas source 82 or liquid source 84 may be input into enclosed space 17 of wound interface 15 to increase pressure $p_0$ from $p_{min}$ toward $p_{max}$.

Wound therapy apparatus 10 may include various fluid conveyances, for example hoses, pipes, valves, tubing, connectors, pressure regulators, and various other fittings, operatively communicating with valve 88, pump 89, pressure sensor 91, gas source 82, liquid source 84, and with ports 42, 44 of wound interface 15 (see FIG. 1B) to communicate gas 83 and liquid 85 from gas source 82 and liquid source 84, respectively, to controller 80 and to communicate input fluid 16 and output fluid 18 between enclosed space 17 of wound interface 15 and controller 80.

In some implementations, at least portions of the output fluid such as exudate 19 (see FIG. 4A) may be trapped in absorbent materials within wound interface 15, and wound interface 15 is replaced as needed. In other implementations, output fluid 18 passes to canister 81 where exudate 19 or liquid, such as liquid 85, is trapped within cavity 99 of canister 81. Gaseous portions of output fluid 18 may then be discharged to the atmosphere from controller 80.

Figure 1B:
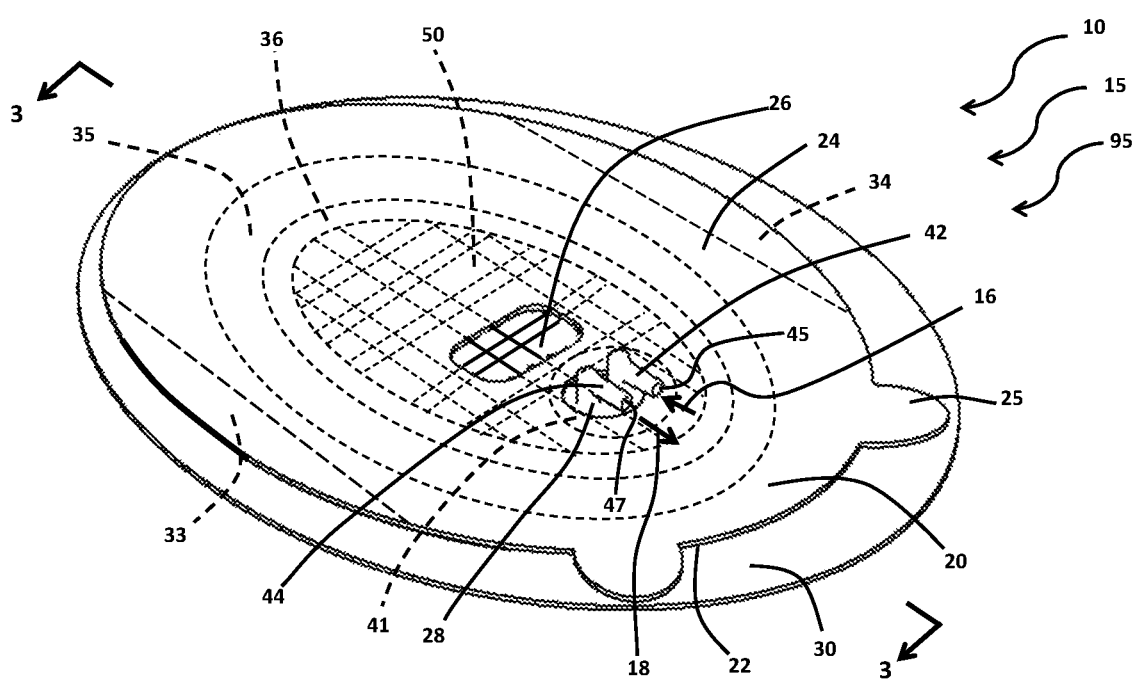
FIG. 1B illustrates by perspective view portions of the exemplary implementation of a wound therapy apparatus of FIG. 1A.

As illustrated in FIG. 1B, wound interface 15 of wound therapy apparatus 10 includes members 20, 30, wings 33, 34, band 35, ports 42, 44, and dressing 50 in first stage of deployment 95. Wings 33, 34, and liner 30 are peelingly, removably secured to adhesive layer 90 (see FIG. 3), which is interposed between liner 30 and member 20 on distal side 22 of member 20, in this implementation of wound interface 15. Removal of liner 30 from securement to adhesive layer 90 and removal of wings 33, 34 from securement to adhesive layer 90 exposes adhesive layer 90 to allow member 20 along with band 35, dressing 50, and ports 42, 44 to be affixed to a skin surface, such as skin surface 11 (see FIG. 4) by the exposed adhesive layer 90. Tabs, such as tab 25, grippable by a user are disposed about member 20 to ease separating liner 30 or wings 33, 34 from member 20 or when applying adhesive layer 90 to skin surface 11.

Figure 3:
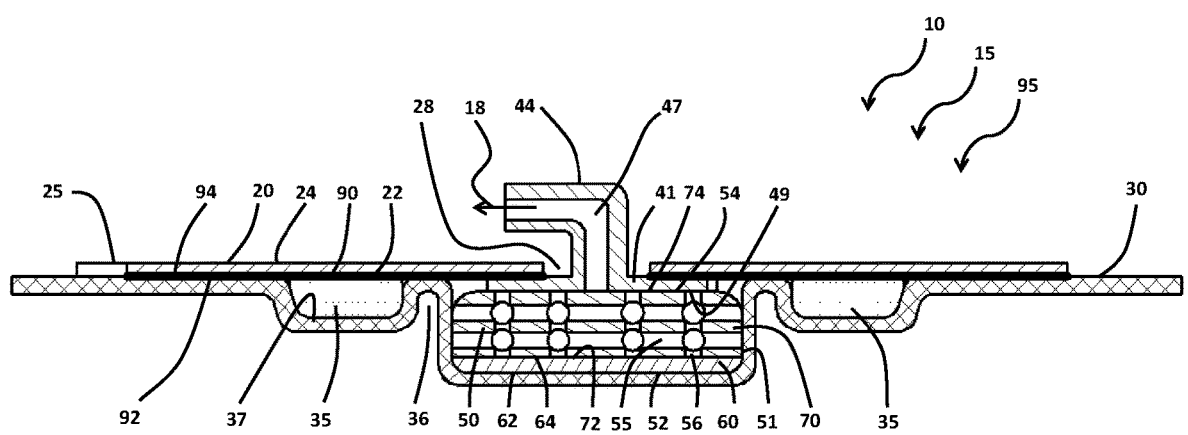
FIG. 3 illustrates portions of the exemplary wound therapy apparatus of FIG. 1 in a first stage of deployment by a cross-section view through section 3-3 of FIG. 1B.
Figure 4A:
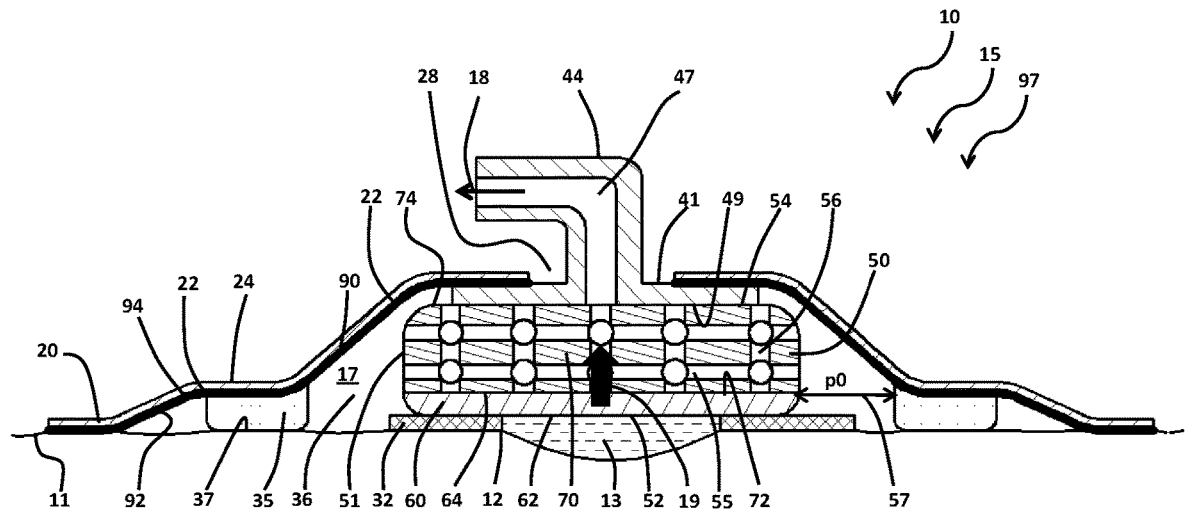
FIG. 4A illustrates portions of the exemplary wound therapy apparatus of FIG. 1 in a second stage of deployment by a cross-section view through section 3-3 of FIG. 1B.

As illustrated in FIGS. 1B, 3 and 4A, ports 42, 44 extend forth from proximal side 24 of member 20 for input of input fluid 16 into enclosed space 17 through lumen 45 of port 42 and withdrawal of output fluid 18 from enclosed space 17 through lumen 47 of port 44. Lumen 45, 47 fluidly communicate with enclosed space 17 through ports 42, 44, respectively, in this implementation. Ports 42, 44 are mounted to flange 41, and portions of flange 41 are secured to distal side 22 of member 20 so that ports 42, 44 extend through aperture 28 in member 20 between distal side 22 and proximal side 24, as illustrated. In this implementation, flange 41 is sized to have a larger diameter than the diameter of aperture 28 to allow securement of portions of flange 41 to distal side 22 of member 20.

Controller 80 communicates fluidly with enclosed space 17 of wound interface 15 through lumen 45, 47 of ports 42, 44, respectively, as illustrated. Controller 80 may monitor or control pressure $p_O$ within enclosed space 17, the input of input fluid 16 into enclosed space including dressing 50 through lumen 45 of port 42, and the withdrawal of output fluid 18 from enclosed space 17 including dressing 50 through lumen 47 of port 44. Tubing may be attached to ports 42, 44, in this implementation, for the communication of input fluid 16 through lumen 45 or output fluid through lumen 47.

Wound interface 15 of wound therapy apparatus 10, as illustrated in FIG. 1B, includes dressing 50 in securement about portions of distal side 22 of member 20. Dressing 50 is in fluid communication with lumen 45, 47 of ports 42, 44, respectively, to exchange input fluid 16 and output fluid 18, in this implementation. Ports 42, 44 may be in proximity to each other or located near diametrically opposite ends of wound interface 15, in various implementations. Member 20, as illustrated, may include window 26, which is formed of transparent material, and a user may view dressing 50 from proximal side 24 of member through window 26, for example, to ascertain the state of dressing 50, such as degree of exudate absorption. Various other implementations may either include windows extending a greater length of the dressing or multiple windows, such as window 26, or window 26 may be omitted.

Band 35 is secured to distal side 22 of member 20 around the circumference of dressing 50 as illustrated, and dressing 50 lies within region 36 bordered by band 35, as illustrated. Band 35 may further ensure a fluid-tight enclosed space 17 around wound bed 13 (see FIG. 4A). Band 35 may be omitted in certain implementations of wound interface 15.

Member 20 may be formed, for example, of polyurethane or polyethylene. The entirety of member 20 may be transparent, or member 20 may be skin toned. Liner 30 and wings 33, 34 may be formed of any of a variety of liner materials such as release-coated paper or plastic film. Ports 42, 44 and flange 41 may be formed of a variety of suitable polymers such as polystyrene, polyethylene or polypropylene. Band 35 may be formed, for example, of hydrocolloid or similar deformable adhesive that may conform to a contour of the skin surface 11 around wound bed 13. Adhesive layer 90 may be formed, for example, of acrylic, silicone adhesive, or hydrocolloid resins suitable for medical use.

Wound interface 15 of wound therapy apparatus 10 is illustrated as being ovoid in shape. Other implementations of wound interface 15 may have other shapes such as circular, square, and rectangular. Band 35 and region 36 defined by band 35 are illustrated as being circular in general conformance to the shape of wound interface 15 of wound therapy apparatus. Band 35 and region 36 may have other shapes or combinations of shapes that may or may not conform to the shape of wound interface 15, in various other implementations.

Figure 2:
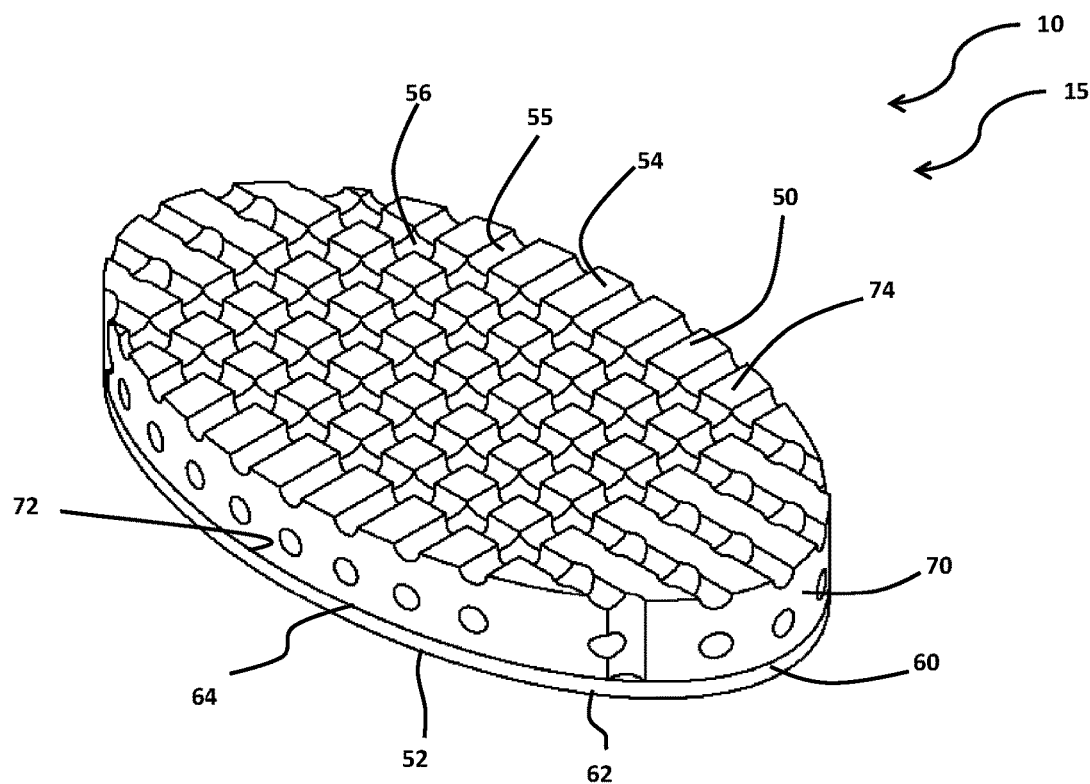
FIG. 2 illustrates by perspective view portions of the exemplary wound therapy apparatus of FIG. 1A.

FIG. 2 illustrates dressing 50 of wound interface 15. As illustrated in FIG. 2, dressing 50 includes distal layer 60 and proximal layer 70, and proximal side 64 of distal layer 60 is joined to distal side 72 of proximal layer 70 to form dressing 50. Proximal side 74 of proximal layer 70 forms proximal side 54 of dressing 50, and distal side 62 of distal layer 60 forms distal side 52 of dressing 50, as illustrated in FIG. 2.

Distal layer 60 may be formed, at least in part, of hydrophobic material, such as polyester fibers, to transfer exudate 19 (see FIG. 4A) away from the wound bed 13 from distal side 62 to proximal side 64 and, thence, into proximal layer 70 through distal side 72. Distal layer 60 may be formed of a Jersey knit of predominantly polyester-type fiber to be woven with predominantly hydrophilic nylon-type fibers of dressing 50. Distal layer 60 may engage various portions of proximal layer 70 or may extend around various portions of proximal layer 70.

Proximal layer 70 may be formed, at least in part, of hydrophilic material such as polyamide fibers to transfer exudate 19 from distal side 72 to proximal side 74 and thence into lumen 47 of port 44 for removal from enclosed space 17 including dressing 50. Proximal layer 70 may also be made of absorbent foams such as polyvinyl alcohol (PVA) or polyurethane (PU). Channels, such as channel 55, pass through proximal layer 70 generally parallel to distal side 49 of flange 41 (see FIGS. 3, 4A) to communicate input fluid 16 or output fluid 18 within proximal layer 70. Channels, such as channel 56, pass between distal side 72 and proximal side 74 of proximal layer 70 to convey input fluid 16 or output fluid 18 between distal side 72 and proximal side 74 of layer 70. Proximal side 54 of dressing includes channels, such as channel 55, as illustrated, to convey output fluid 18 from proximal layer 70 into lumen 47 of port 44 or to distribute input fluid 16 from lumen 45 of port 42 about the proximal side 74 of proximal layer 70. Channels, such as channel 55, 56, may be of any geometric shape including slits, in various implementations. Any number of channels may be formed in proximal layer 70 and may have various distributions, orientations, spatial relationships and interconnectivity, in various implementations. Some implementations of proximal layer 70 may include only channels, such as channel 56, between distal side 72 and proximal side 74. Other implementations of proximal layer 70 may include only channels, such as channel 55, generally parallel to distal side 49 of flange 41. Still other implementations of proximal layer 70 may entirely omit channels, such as channels 55, 56. Yet other implementations of proximal layer 70 may include only channels, such as channel 55, generally parallel to distal side 49 of flange 41 in the proximal side 74 of proximal layer 70 to communicate fluidly between proximal side 74 and lumen 45, 47.

FIG. 3 illustrates wound interface 15 of wound therapy apparatus 10 in a first stage of deployment 95 with liner 30 secured to member 20 by adhesive layer 90 to cover the distal side of wound interface 15 including at least portions of distal side 92 of adhesive layer 90, distal side 37 of band 35, and distal side 52 of dressing 50 which allows the user to manipulate wound interface 15 without becoming engaged with adhesive layer 90 in first stage of deployment 95 and also protects dressing 50 from contamination.

As illustrated in FIG. 3, proximal side 94 of adhesive layer 90 is secured to distal side 22 of member 20, and flange 41 is biased against distal side 92 of adhesive layer 90 to secure flange 41 to member 20. Flange 41 may be secured to distal side 22 of member 20 in other ways, in other implementations. At least portions of dressing 50 proximate proximal side 54 are positioned within circumscribed region 36, as illustrated. In other implementations, the entirely of dressing 50 from proximal side 54 to distal side 52 lies within region 36. In still other implementation, band 35 and, hence, region 36 is omitted. Side 51 (FIG. 4A) of dressing 50 may be set apart from band 35 by gap 57 to allow for expansion of dressing 50 without affecting sealing that may be provided by band 35 in this implementation.

As illustrated in FIG. 3, proximal side 54 of bandage 50 is engaged with flange 41. Proximal side 54 of bandage 50 is in fluid communication with lumen 45, 47 of ports 42, 44 respectively, in this implementation. Various channels, such as channel 55, may be formed in proximal side 54 of bandage 50, in distal side 49 of flange 41 (not shown), or in both proximal side 54 of bandage 50 and distal side 49 of flange 41 to convey input fluid 16 and/or output fluid 18 between proximal side 54 of bandage 50 and lumen 45, 47 of ports 42, 44, respectively FIG. 4A illustrates wound interface 15 of wound therapy apparatus 10 in second stage of deployment 97. In second stage of deployment 97, liner 30 and wings 33, 34 have been removed, and wound interface 15 is secured to skin surface 11 by at least portions of distal side 92 of adhesive layer 90 exposed by removal of liner 30 and wings 33, 34, as illustrated. The user may selectively remove portions of liner 30 or wings 33, 34 in order to expose only a portion of adhesive layer 90, so that the user may focally anchor wound interface 15 adhesively to the skin surface 11. Portions of member 20 may flex to conform to skin surface 11 when portions of adhesive layer 90 are secured to skin surface 11, as illustrated. Adhesive layer 90 may be secured to skin surface around the perimeter of wound interface 15 to form a fluid-tight seal between wound interface 15 and skin surface 11. In certain implementations that include band 35, this optional annulus of thick deformable adhesive forms a fluid-tight seal between distal side 37 of band 35 and skin surface 11 around the circumference of wound interface 15. In implementations that omit band 35, adhesive layer 90 is secured to skin surface around the perimeter of wound interface 15 to form a fluid-tight seal between wound interface 15 and skin surface 11. Both adhesive layer 90 and band 35 may form a fluid-tight seal between wound interface 15 and skin surface 11, in some implementations.

The user may, for example, manually grasp member 20 in first stage of deployment 95 and may then peelingly remove liner 30 from distal side 92 of adhesive layer 90 to expose those portions of distal side 92 of adhesive 90 attached to liner 30 as well as distal side 37 of band 35, in this implementation. With liner 30 removed, the user may then position wound interface 15 with respect to the wound bed 13 and then bias compressibly distal side 92 of adhesive layer 90 and distal side 37 of band 35 against skin surface 11 to secure wound interface 15 to skin surface 11. The user may manipulate the wound interface 15 by gripping wings 33, 34 or tabs, such as tab 25, when peelingly removing liner 30 or when positioning and then compressibly biasing at least portions of distal side 92 of adhesive layer 90 exposed by removal of liner 30 and distal side 37 of band 35 against skin surface 11. The user may then remove wings 33, 34 from engagement with distal side 92 of adhesive layer 90 and then bias compressibly these portions of distal side 92 of adhesive layer 90 exposed by the removal of wings 33, 34 against skin surface 11 to further secure wound interface 15 to skin surface 11 and, thus, form fluid-tight enclosed space 17. Member 20 or band 35 may flex to conform to skin surface 11 in order to bias band 35 against skin surface 11. Band 35 when biased against skin surface 11 may form a fluid-tight seal between distal side 37 of band 35 and skin surface 11 around the circumference of wound interface 15.

With wound interface 15 secured to skin surface 11 to form enclosed space 17 over wound bed 13 in second stage of deployment 97, as illustrated in FIG. 4A, input fluid 16 may be input into enclosed space 17 through lumen 45 of port 42 and output fluid 18 may be withdrawn from enclosed space 17 through lumen 47 of port 44 by controller 80, as illustrated, to vary pressure $p_0$ within enclosed space 17 over a pressure cycle generally having a pressure range $p_{min} \leq p_0 \leq p_{max}$ where $p_{min}$ is the minimum pressure over the pressure cycle and $p_{max}$ is the maximum pressure over the pressure cycle. Other implementations may have a single port, such as port 42, 44, with a single lumen, such as lumen 45, 47, and both the input fluid, such as input fluid 16, and the output fluid, such as output fluid 18, pass through the single lumen of the single port.

Input fluid 16 may include gas, such as gas 83, liquid, such as liquid 85, or combinations of gas and liquid. In various implementations, input fluid 16 is a gas having an $O_2$ concentration greater than atmospheric air. In various implementations input fluid 16 may be medical grade oxygen. In various other implementations, input fluid 16 may be a liquid that may have some therapeutic benefit, such as saline irrigation, an antibiotic, or an analgesic.

As illustrated in FIG. 4A, exudate 19 is withdrawn through distal layer 60 away from the wound bed 13. Exudate 19 is withdrawn from distal side 62 to proximal side 64 of distal layer 60 and thence into proximal layer 70 through distal side 72, from distal side 72 to proximal side 74, and from proximal side 74 into lumen 47 of port 44 for withdrawal away from the wound bed. Depending on intended use, the wound interface 15 may be discarded and replaced when dressing 50 is deemed to approach absorbent capacity, or continued suction may be applied to apparatus 15 to transfer output fluid 18 including exudate 19 from enclosed space 17 including dressing 50 to canister 81 (See FIG. 1A)

Output fluid 18 may include air withdrawn from enclosed space 17. Output fluid 18 may include input fluid 16 as input fluid 16 is withdrawn from enclosed space 17 in order to vary the pressure $p_0$ periodically over the pressure cycle.

Figure 4B:
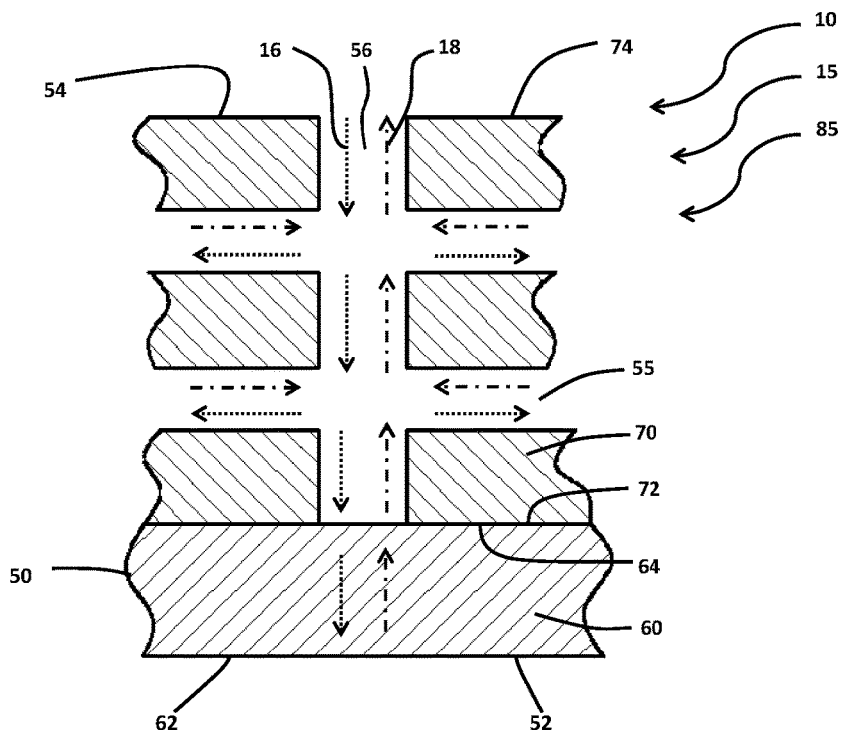
FIG. 4B illustrates by cross-sectional view portions of the exemplary wound therapy apparatus of FIG. 1A.

As illustrated in FIG. 4B, channels, such as channel 56 that pass through proximal layer 70 between distal side 72 and proximal side 74 may communicate input fluid 16 through proximal layer 70 from proximal side 74 to distal side 72, into distal layer 60, and the input fluid 16 may pass through distal layer 60 to wound bed 13. Channels, such as channel 55 may communicate input fluid 16 laterally throughout proximal layer 70 of dressing to distribute evenly the input fluid 16 over layer 60 and, thus, wound bed 13. Channels, such as channel 55, 56 may communicate output fluid 18 laterally through proximal layer 70 and from distal side 72 to proximal side 74, respectively, to allow withdrawal of output fluid 18 from the entirety of wound bed 13 and dressing 50, as illustrated in FIG. 4B. Output fluid may be communicated from wound bed 13, through distal layer 60, thence through proximal layer 70 to spread throughout proximal layer 70 or be withdrawn from proximal layer 70 via lumen 47.

Figure 4C:
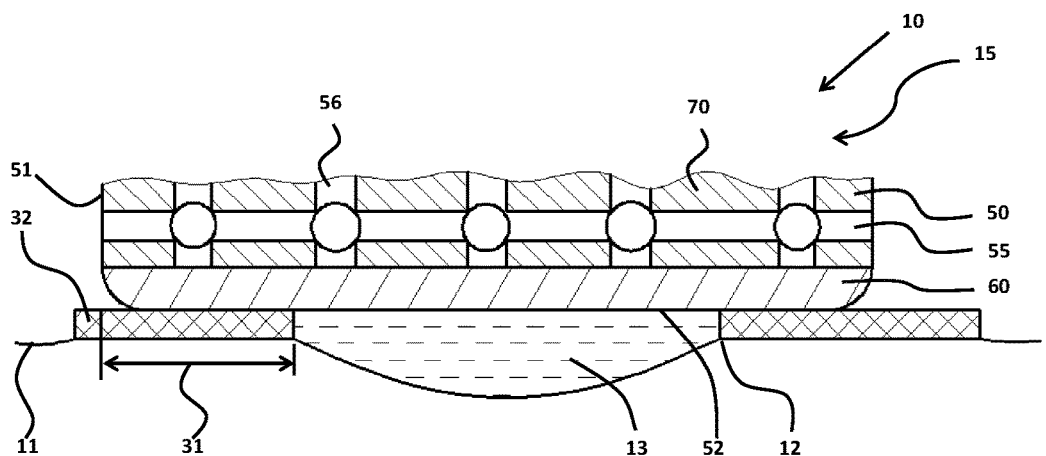
FIG. 4C illustrates by cross-sectional view portions of the exemplary wound therapy apparatus of FIG. 1A.

Since the overlapping of dressing over the wound bed 13 onto skin surface 11 may result in maceration of skin surface 11, and because it is tedious to trim a dressing to the exact geometric outline of the wound bed 13, a method for maximizing absorbent capacity while avoiding the maceration problem is taught herein. FIG. 4C illustrates distal end 52 of dressing 50 biased against wound bed 13 and skin surface 11 with wound therapy apparatus 10 including wound interface 15 in second stage of deployment 97. As illustrated in FIG. 4C, side 51 of dressing 50 extends past wound boundary 12 of wound bed 13 by length 31 to engage portions of distal side 52 with skin surface 11 while other portions of distal end 52 are biased against wound bed 13.

Thus dressing 50 including distal end 52 is not fitted to match wound bed 13, in this implementation, and the perimeter of dressing 50 at distal end 52 extends beyond wound boundary 12. To prevent maceration of skin from prolonged contact with dressing 50 that may be moist with exudate, a water-impermeable skin-protective polymer film is created by painting or applying a layer of suitable polymer 32 over the peri-wound skin that would be subject to such prolonged contact with a moist dressing. One solution is use a cyanoacrylate class of liquid adhesive such as 2-octyl cyanoacrylate. Another solution is to paint a formulation of quick drying ethyl acetate over the peri-wound surface.

Figure 5:
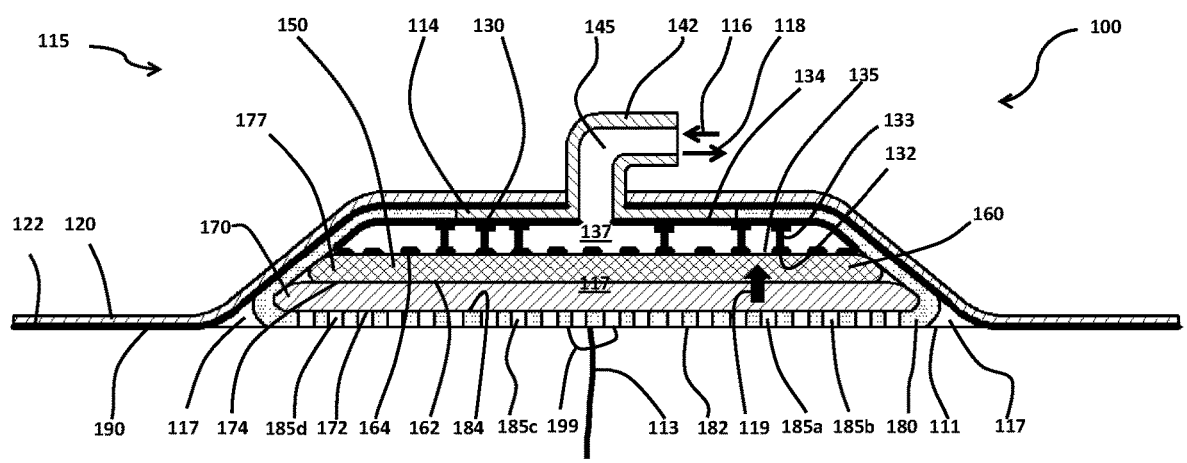
FIG. 5 illustrates by cross-sectional view a second exemplary implementation of a wound therapy apparatus.

FIG. 5 illustrates exemplary wound therapy apparatus 100 including wound interface 115. As illustrated in FIG. 5, wound interface 115 includes member 120 with adhesive layer 190 coated on at least portions of distal surface 122 of member 120 for securing the member 120 to skin surface 111. When secured to skin surface 111 around the perimeter of member 120 by adhesive 190, wound interface 115 encloses wound bed 113 at skin surface 111 within enclosed space 117 that is fluid-tight. As illustrated in FIG. 5, port 142 is secured to member 120 by flange 114 that is adhesively secured to member 120 by portions of adhesive layer 190. Port 142 allows fluid communication with enclosed space 117 by lumen 145. A controller, such as controller 80 of wound therapy apparatus 10, may communicate input fluid 116 into enclosed space 117 via lumen 145 of port 142 and withdraw output fluid 118 from enclosed space 117 through lumen 145 of port 142, for example, to vary $p_0$ within enclosed space 117 periodically over a pressure cycle generally having a pressure range $p_{min} \leq p_0 \leq p_{max}$ where $p_{min}$ is the minimum pressure over the pressure cycle and $p_{max}$ is the maximum pressure over the pressure cycle. Member 120 may be formed of various polymer layer(s) or woven material(s). Input fluid 116 may be liquid, gas, or combinations of liquid and gas, such as liquid 85 and gas 83, and input fluid 116 may have an $O_2$ concentration greater than that of atmospheric air. Withdrawal of output fluid 118 through lumen 145 of port 142 may draw exudate 119 from wound bed 113 into layer(s), such as layers 160, 170, within wound interface 115, and the layers may absorb exudate 119.

As illustrated in FIG. 5, dressing 150 of wound therapy apparatus 100 includes proximal layer 160, intermediary layer 170, and distal layer 180 within enclosed space 117, and dressing 150 is secured to member 120 to form a part of wound interface 115. Various numbers of layers, such as layers 160, 170, 180, may be included in other implementations of wound interface 115, and the layer(s) may be arranged in various ways. Certain implementations of wound interface 115 may include only distal layer 180. Portions of distal layer 180, as illustrated, are secured to distal side 122 of member 120, with or without any wraparound, and portions of distal side 182 of distal layer 180 are biased against skin surface 111 and wound bed 113. Intermediary layer 170 is biased between distal layer 180 and proximal layer 160 with distal side 172 of intermediary layer 170 biased against proximal side 184 of distal layer 180, and proximal side 174 of intermediary layer 170 biased against distal side 162 of proximal layer 160. Proximal layer 160 is biased between layer 170 and spacer 130 with proximal side 164 of proximal layer 160 biased against distal side 132 of spacer 130, as illustrated.

Spacer 130 is secured to member 120 by securement of proximal side 134 of spacer 130 to distal side 122 of member 120 within enclosed space 117, in this implementation. Spacer 130 defines plenum 137 within spacer 130, and spacer 130 maintains proximal layer 160, intermediary layer 170, and distal layer 180 in biased engagement with one another, as illustrated. Spacer 130 may generally be a bilayer polymer structure with or without additional distribution channels that may be created by focal welds 133 of distal side 132 to proximal side 134 to limit distension of the plenum 137 under positive pressure ($p_o$>$p_{amb}$). The purpose of spacer 130, in this implementation, is to disperse input fluid 116 via plenum 137 across proximal side 164 of layer 160 and thus disperse input fluid 116 over wound bed 113. Spacer 130 may also have the purpose of facilitating removal of exudate 119 or other fluids during withdrawal of output fluid 118. Spacer 130 may have a variety of shapes and sizes ranging from circular, rectangular, ovoid, etc., with a footprint that substantially approximates that of proximal side 164 of layer 160. Spacer 130 may be omitted in some implementations of wound interface 115, or functionally be substituted by surface structures in adjacent layers such as that of dressing 50 illustrated in FIG. 2.

Lumen 145 passes through port 142 and through proximal side 134 of spacer 130 into plenum 137, and input fluid 116 or output fluid 118 may be communicated between plenum 137 and lumen 145. For example, input fluid 116 may enter plenum 137 through lumen 145, and then disperse within plenum 137 so that essentially the same pressure $p_o$ exists throughout plenum 137. Input fluid 116 may then flow from plenum 137 through spacer passages, such as spacer passage 135, in distal side 132 of spacer 130 into proximal layer 160 through proximal side 164. The spacer passages may be evenly distributed over distal side 132 of spacer 130 so that input fluid 116 is evenly distributed over proximal side 164 of proximal layer 160 from plenum 137 (see FIG. 6A). Input fluid 116 may then flow through proximal layer 160, through intermediary layer 170, and through fenestrations, such as fenestrations 185a, 185b, 185c, 185d (see FIG. 6B), in distal layer 180, to contact wound bed 113 as well as skin surface 111. The fenestrations 185a, 185b, 185c, 185d, which may vary in number, aperture shape, and size, pass between proximal side 184 and distal side 182 of distal layer 180, may be evenly distributed over the wound contact surface of distal layer 180 so that input fluid 116 is evenly distributed over skin surface 111 and wound bed 113.

The thickness between proximal side 184 and distal side 182 of distal layer 180 may range from about 0.1 mm to about 2 mm, in certain implementations. The thickness between proximal side 184 and distal side 182 of distal layer 180 may range from about 0.2 mm to about 1 mm, in certain implementations. In various implementations, the size of fenestrations 185a, 185b, 185c, 185d may generally range from about 250 microns to 2500 microns in diameter or equivalent, or from about 500 microns (#35 Mesh) to about 1000 microns (#18 Mesh) in diameter or equivalent. In various implementations, the size of fenestrations 185a, 185b, 185c, 185d may generally range from about 50 microns (#270 Mesh) to about 1000 microns (#18 Mesh) in diameter or equivalent, or from about 100 microns (#140 Mesh) to about 750 microns (about #22 Mesh) in diameter or equivalent. The number of fenestrations, such as fenestrations 185a, 185b, 185c, 185d, per $cm^2$ in distal layer 180 may generally range from about 45 per $cm^2$ to about 2500 per $cm^2$, in certain implementations. The number of fenestrations, such as fenestrations 185a, 185b, 185c, 185d, per $cm^2$ in distal layer 180 may range from about 25 per $cm^2$ to about 200 per $cm^2$, in certain implementations.

Thus, for example, input fluid 116 may provide enhanced $O_2$ exposure to wound bed 113 and to skin surface 111. Pressure $p_o$ exists generally throughout enclosed space 117 including wound bed 113 and skin surface 111 because input fluid 116 and output fluid 118 may flow throughout enclosed space 117 including through proximal layer 160, intermediary layer 170, distal layer 180, and through spacer 130. In other implementations, layer 180 may, for a simpler design, be attached to adhesive layer 190 horizontally, in substantially the same plane as skin layer 111. Spacer 130, and multiple layers of material are optional features of wound interface 115.

Exudate 119 may flow from wound bed 113 through perforations, such as perforation 185a, 185b, 185c, 185d, in distal layer 180 into intermediary layer 170, from intermediary layer 170 into proximal layer 160, and from proximal layer 160 through spacer passages, such as spacer passage 135, into plenum 137. Output fluid 118 including exudate 119 and input fluid 116 may flow through distal layer 180, intermediary layer 170, and proximal layer 160 through spacer passages 135 into plenum 137, and output fluid 118 may be withdrawn from plenum 137 through port 142 via lumen 145, in this implementation.

As illustrated in FIG. 5, wound bed 113 has the form of an incision with stitch 199. Distal layer 180 is formed of a perforated sheet of silicone including polydimethylsiloxane. Silicone may include other non-stick polymers such as, for example, polyethylene terephthalate (PET), polytetrafluoroethylene (PTFE), or other fluoropolymers. While silicone is known to have salutary effects in reducing the prominence of hypertrophic or otherwise already formed scars, the use of silicone sheeting with perforations, such as perforations 185a, 185b, 185c, 185d, to modulate scar formation contemporaneously as a wound 113 heals is disclosed herein. Note that, silicone is impervious to exudate transfer and for a weeping wound, such occlusion can result in skin maceration and other untoward effects. Inclusion of perforations, such as perforations 185a, 185b, 185c, 185d, in distal layer 180 may allow exudate transfer and absorption away from the wound bed 113. Thus, wound therapy apparatus 100 may be used at the very inception of the healing process continuing to completion, so that there may be no or less need to revise a prominent scar later, after the scar has already suboptimally formed.

Wound bed 113, as illustrated, is fresh and about to begin the healing process of forming a scar. Normally, applying a liquid-impermeable layer of silicone against a fresh wound bed such as wound bed 113 that likely has a significant degree of exudation would risk skin maceration. However, wound interface 115 includes fenestrations, such as fenestrations 185a, 185b, 185c, 185d, in the silicone sheet that forms distal layer 180 and provides for absorbtion of exudate and/or transfer of exudate on the proximal side 184 of distal layer 180, to prevent maceration of skin surface 111. In this illustrated implementation, distal layer 180 comprising perforated silicone is used to prophylactically prevent prominent scar formation, not to treat a scar that has already formed. Of course, wound bed 113 may be any type of wound bed, in various other implementations. Fenestrations, such as fenestration 185a, 185b, 185c, 185d, allow fluid exchange with wound bed 113 and skin surface 111 through distal layer 180, which may, for example, prevent maceration of skin 111. Distal layer 180, in particular distal side 182 thereof, may be impregnated with various medicaments such as steroids, hormones or other drugs in controlled release form.

Healing of an incisional wound, such as wound bed 113, with little or no visible scar formation may require, inter alia, adequate blood flow, oxygenation, absence of infection, proper moisture balance, and an even apposition (alignment) of wound edges with a homogenous dispersion of tension across the entire wound area. The classic ugly "railroad track" scar may be caused by focal tension exerted by a limited number of suture lines, which can be worsened yet further by a certain degree of wound inflammation, swelling and dehiscence (wound edge separation). Given the high coefficient of friction of silicone with the skin surface 111, distal layer 180 of wound therapy apparatus 100, which may be formed of silicone, may secure the spatial relationship of one side of the incision with the other and resist shear and relative movement. This may minimize the risk of an uneven-tension-induced scar by harmonizing and homogenizing the wound tension over the incision line, as if, for example, hundreds more tiny sutures are at work. The use of perforated silicone for distal layer 180 may also (1) prevents skin maceration by preventing fluid buildup over the skin and effectively keeping intermediary layer 170, which may be damp, from prolonged contact with peri-wound skin, and (2) selectively transfers exudate away from wound and (3) decreases the lateral wound tension and stress on the suture line by even force and neutralization of focal shear, thereby decreasing risk of dehiscence, graft failure and prominent scar formation.

Intermediary layer 170 may include medicament 177, such as amniotic fluid or bone morphogenetic protein (BMP) or other scar modulating healing factors, and medicament 177 may be delivered over time from layer 170 to the wound bed 113 by fluid communicated through intermediary layer 170 and distal layer 180. Layer 170 may be made of alginate-like substance impregnated with the medicament 177, and layer 170 may be configured to deliver the medicament 177 to wound bed 113 in a controlled release manner.

Figure 6A:
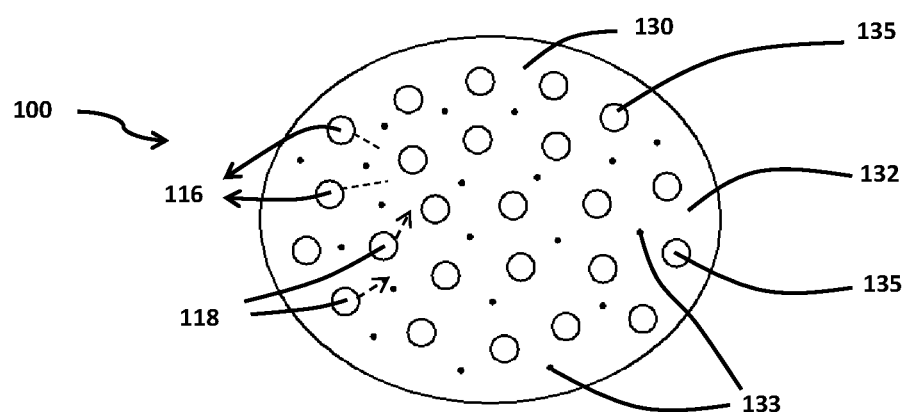
FIG. 6A illustrates by plan view portions of the exemplary wound therapy apparatus of FIG. 5.

Layer 160 may be made of a variety of materials including cotton gauze, polyester or polyamide fibers, or open-cell foams of polyurethane or polyvinyl alcohol. Closed cell polyurethane foam may be used when formulations of polyethylene glycol (PEG) is added to the polyurethane to render the matrix itself highly absorbent, fluid conductive and tissue biocompatible. These materials may aid in transfer of the exudate 119 from wound bed 113 to lumen 145. Layer 160 may include a super absorbent polymer such as sodium polyacrylate, FIG. 6A illustrates distal side 132 of spacer 130 including spacer passages such as spacer passage 135. Spacer passages, such as spacer passage 135, communicate input fluid 116 and output fluid 118 between distal side 132 and plenum 137, in this implementation. Although illustrated as circular, spacer passages 135 may have a square, circular, rectangular, slit, or other cross section, in various implementations.

Figure 6B:
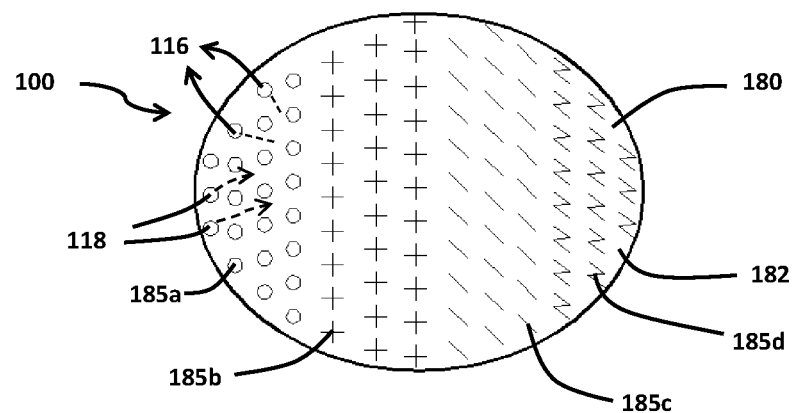
FIG. 6B illustrates by plan view portions of the exemplary wound therapy apparatus of FIG. 5.

FIG. 6B illustrates distal side 182 of distal layer 180 including fenestrations, such as fenestrations 185a, 185b, 185c, 185d that have circular, cross slit, linear slit, and jig-zag slit cross sections, respectively. The fenestrations may have other geometries, in other implementations. The fenestrations extend between distal side 182 and proximal side 184 to communicate input fluid 116 and output fluid 118 between distal side 182 and proximal side 184 of distal layer 180, in this implementation.

Figure 7:
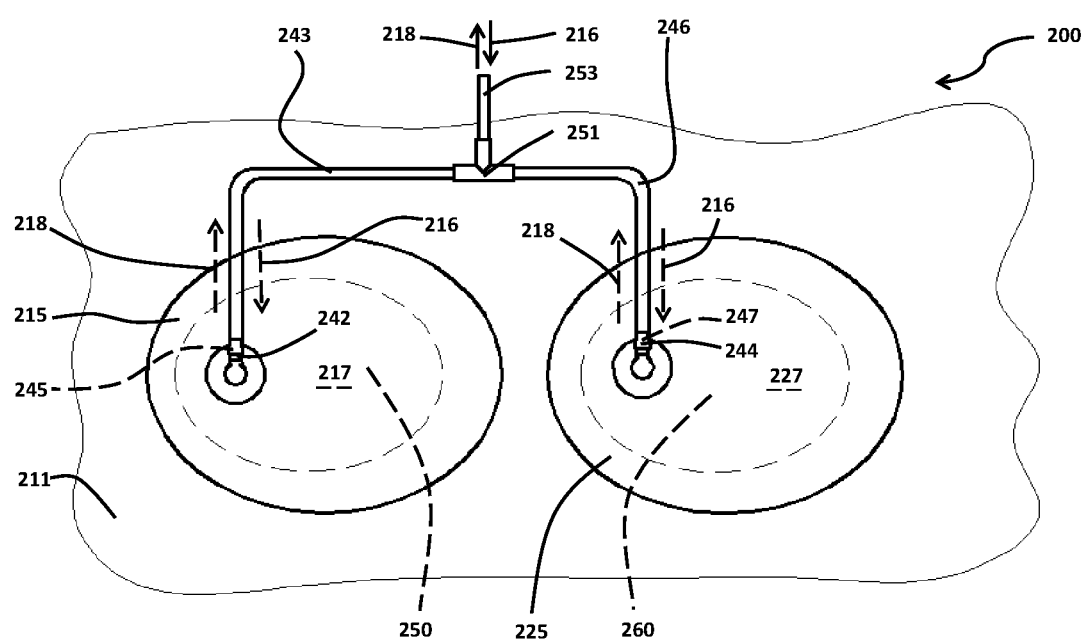
FIG. 7 illustrates by plan view a third exemplary implementation of a wound therapy apparatus.

FIG. 7 illustrates wound therapy apparatus 200 including wound interfaces 215, 225 secured to skin surface 211. Wound interfaces 215, 225 may include dressings 250, 260 disposed in enclosed spaces 217, 227, respectively. Enclosed spaces 217, 227 defined by wound interfaces 215, 225, respectively, are fluid-tight, in this implementation, and dressings 250, 260 may include two or more layers, such as in dressings 50, 150, 350, 550, 650, 750.

As illustrated in FIG. 7, wound interfaces 215, 225 are operated in parallel. A controller, such as controller 80 of wound therapy apparatus 10, may input the input fluid 216 concurrently into enclosed spaces 217, 227, and withdraw output fluid 218 concurrently from enclosed spaces 217, 227. As illustrated in FIG. 7, tubing 253 is joined to fitting 251 to fluidly communicate with tubing 243, 246, and tubing 243, 246 fluidly communicates with lumen 245, 247 of ports 242, 244, respectively. Accordingly, input fluid 216 may be communicated through tubing 253, through fitting 251, through tubing 243, 246, through lumen 245, 247 of ports 242, 244 into enclosed space 217, 227 of wound interfaces 215, 225, respectively, as illustrated in FIG. 7. Output fluid 218 may be withdrawn from enclosed space 217, 227 of wound interfaces 215, 225, respectively, through lumen 245, 247 of ports 242, 244, respectively, through tubing 243, 246, throughfitting 251, and through tubing 253, as illustrated in FIG. 7. Any number of wound interfaces, such as wound interfaces 215, 225, may be disposed about skin surface 211 that communicate in parallel, in various other implementations. Various configurations of tubing, such as tubing 243, 246, 253 including fittings, such as fitting 251, as well as various connectors and other fluid pathways may be provided, in various implementations.

Figure 8A:
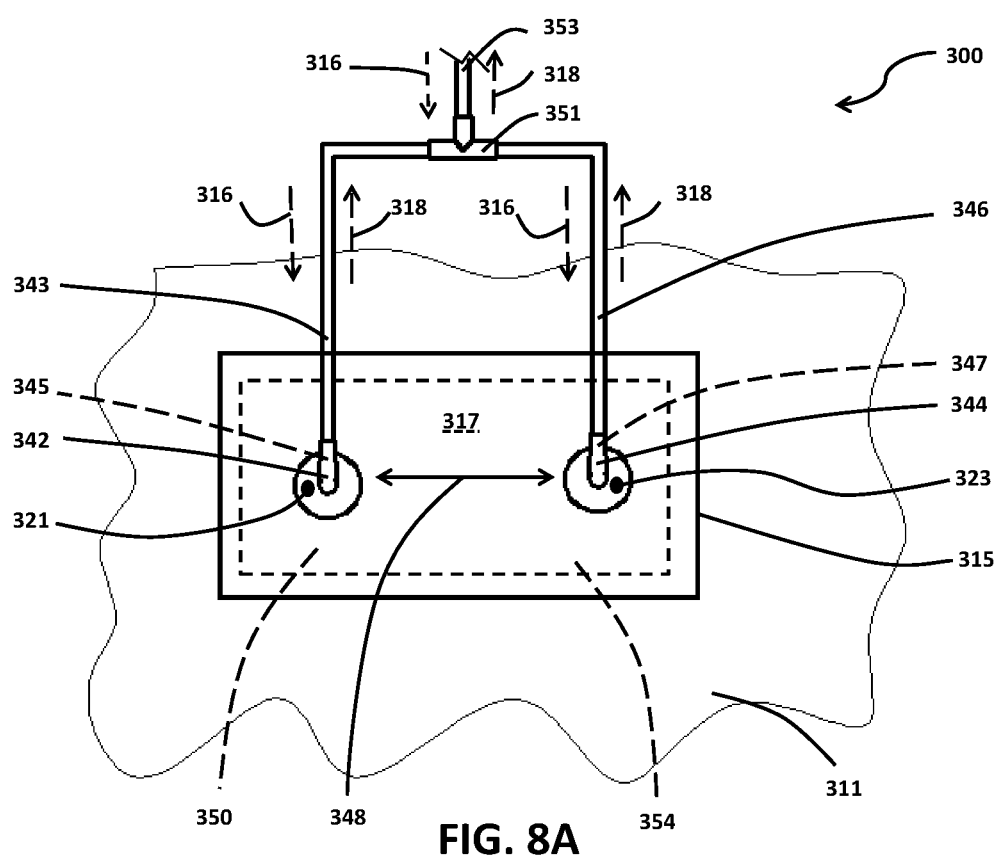
FIG. 8A illustrates by plan view a fourth exemplary implementation of a wound therapy apparatus.

FIG. 8A illustrates portions of exemplary wound therapy apparatus 300 including wound interface 315 affixed to skin surface 311. Wound interface 315, as illustrated, includes member 320 and ports 342, 344 that define lumen 345, 347, respectively, for fluid communication with enclosed space 317 including dressing 350 within enclosed space 317. Ports 342, 344 are disposed about member 320, as illustrated. With wound interface 315 affixed to skin surface 311, wound interface 315 at least in part defines enclosed space 317 that is generally fluid-tight, in this implementation. Dressing 350 may include two or more layers, such as in dressings 50, 150, 250, 550, 650, 750, or may be formed of a single layer. Note that although wound interface 315 and dressing 350 are illustrated as rectangular in exemplary wound therapy apparatus 300, wound interface 315, dressing 350, or both wound interface 315 and dressing 350 may assume various other geometric shapes, such as round, ovoid or square, in various implementations.

Ports 342, 344 are set distance 348 apart from one another, as illustrated, to communicate fluidly with different portions of proximal side 354 of dressing 350 through lumen 345, 347, respectively. Distance 348 may be selected so that input fluid 316 is input generally uniformly over proximal side 354 and output fluid 318 is withdrawn generally uniformly from proximal side 354 of dressing 350 via lumen 345, 347. As illustrated in FIG. 8A, tubing 353 is joined to fitting 351 to fluidly communicate with tubing 343, 346, and tubing 343, 346 fluidly communicate with lumen 345, 347 of ports 342, 344, respectively. Accordingly input fluid 316 may be communicated through tubing 353, through fitting 351, through tubing 343, 346, through lumen 345, 347 of ports 342, 344, respectively, to proximal side 354 of dressing 350 within enclosed space 317, as illustrated in FIG. 8. Output fluid 318 may be withdrawn from proximal side 354 of dressing 350 within enclosed space 317 through lumen 345, 347 of ports 342, 344, respectively, through tubing 343, 346, through fitting 351, and through tubing 353, as illustrated in FIG. 8A. A controller, such as controller 80 of wound therapy apparatus 10, may fluidly communicate with wound interface 315 via tube 353 to input the input fluid 316 concurrently into enclosed space 317 and withdraw output fluid 318 from enclosed space 317. Any number of ports, such as ports 342, 344, may be disposed about wound interface 315 to communicate fluidly with various portions of proximal side 354 of dressing 350 within enclosed space 317, in various other implementations.

Figure 8B:
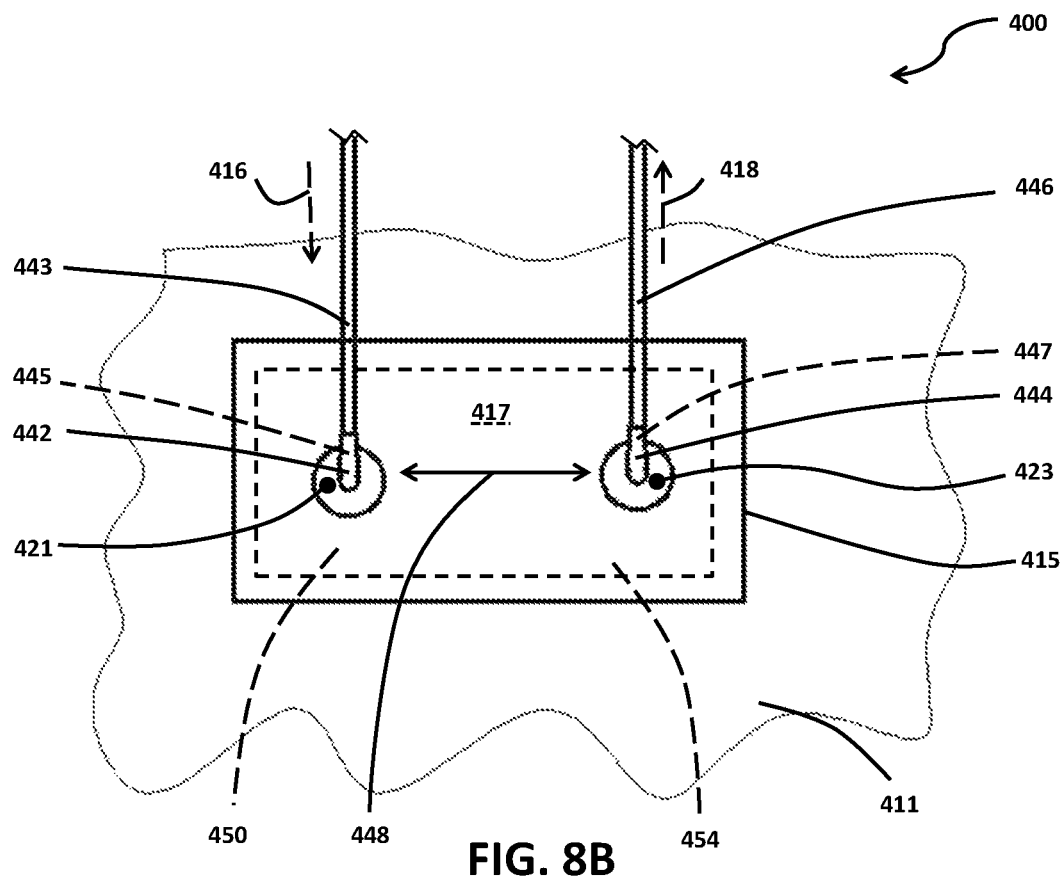
FIG. 8B illustrates by plan view a fifth exemplary implementation of a wound therapy apparatus.

FIG. 8B illustrates portions of exemplary wound therapy apparatus 400 including wound interface 415 affixed to skin surface 411. Wound interface 415, as illustrated, includes ports 442, 444 that define lumen 445, 447, respectively, for fluid communication with enclosed space 417 including dressing 450 within enclosed space 417 by a controller, such as controller 80 of wound therapy apparatus 10. With wound interface 415 affixed to skin surface 411, member 420 at least in part defines enclosed space 417 that is generally fluid-tight, in this implementation.

Ports 442, 444 are set distance 448 apart from one another, as illustrated, to communicate fluidly with different portions of proximal side 454 of dressing 450 through lumen 445, 447, respectively. As illustrated in FIG. 8B, lumen 445, 447 of ports 442, 444, respectively, fluidly communicate with tubing 443, 446. In some implementations, input fluid 416 is input into enclosed space 417 through lumen 445 of port 442 simultaneous with withdrawal of output fluid 418 from enclosed space 417 through lumen 447 of port 444. In other implementations, input fluid 416 is input into enclosed space 417 through lumen 445 of port 442 sequentially with withdrawal of output fluid 418 from enclosed space 417 through lumen 447 of port 444, the input fluid 416 being allowed to dwell within the enclosed space 417. Input fluid 416 and output fluid 418 are liquids, in this implementation. This may provide certain benefits in terms of purging exudate or bioburden and keeping tubing, such as tubing 443, 446, patent. For example, for a wound bed in the lower extremity, the input fluid 416 may enter port 442 that is in a superior location while the output fluid 418 is withdrawn from port 444 that is in an inferior position relative to port 442, and the benefit of gravity is used to advantage to move the waste material and fluid out of the wound area particularly in implementations wherein input fluid 416 and output fluid 418 are liquid, such as liquid 85. Various configurations of tubing, such as tubing 443, 446, including fittings, connectors, and other fluid pathways, may be provided, in various implementations as may depend on the desired effect.

Figure 9:
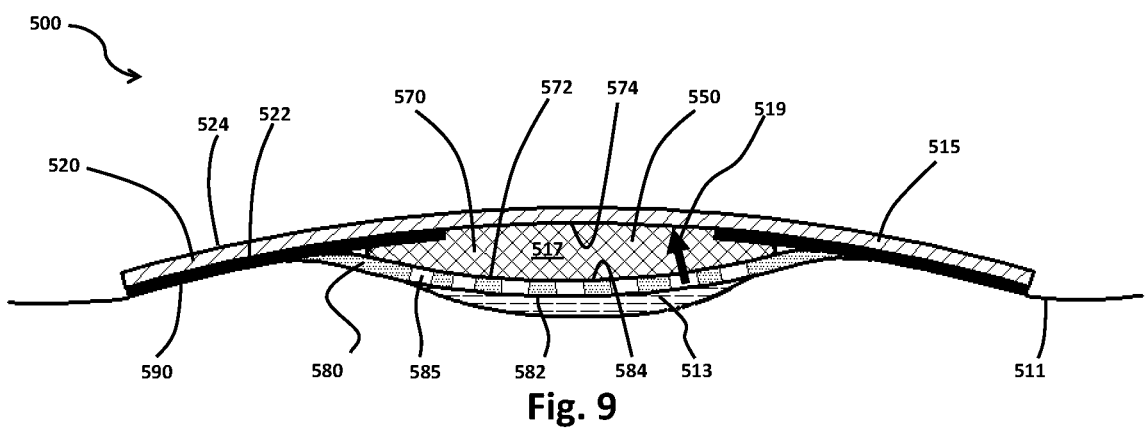
FIG. 9 illustrates by cross-sectional view a sixth exemplary implementation of a wound therapy apparatus.

FIG. 9 illustrates exemplary wound therapy apparatus 500. As illustrated in FIG. 9, wound therapy apparatus 500 includes wound interface 515, and wound interface 515 includes member 520, proximal layer 570, distal layer 580, and adhesive layer 590. As illustrated, wound interface 515 is secured to skin surface 511 by adhesive layer 590 so that distal side 582 of distal layer 580 contacts wound bed 513, and wound interface 515 defines enclosed space 517 over wound bed 513 that includes proximal layer 570, distal layer 580. Proximal layer 570 and distal layer 580 form dressing 550, in this implementation. Enclosed space 517 may be fluid-tight, and there is no lumen passing between distal side 522 and proximal side 524 of member 520, in this implementation.

Proximal layer 570, as illustrated in FIG. 9, is in biased disposition between proximal side 584 of distal layer 580 and distal side 522 of member 520 with proximal side 574 of proximal layer 570 biased against distal side 522 of member 520 and distal side 572 of proximal layer 570 biased against proximal side 584 of distal layer 580. Exudate 519 is withdrawn by capillary action from wound bed 513 through fenestrations, such as fenestrations 585, in distal layer 580 into layer 570 through distal side 572 of layer 570, in this implementation. Layer 570, in this implementation, retains exudate 519. When layer 570 becomes sufficiently saturated with exudate 519, wound interface 515 may be removed and another wound interface similar to wound interface 515 placed over wound bed 513.

Distal layer 580 may be made of silicone including silicone-like material that is perforated, as illustrated. Proximal layer 570 may be made, for example, of polyvinyl alcohol, polyurethane foam, polyurethane foam with polyethylene glycol (PEG) to enhance its water absorption and transport characteristics, or other absorbent materials, such as gauze, that may be impregnated with, for example, chitosan, silver, or a super absorbent polymer such as sodium polyacrylate to retain exudate 519 within layer 570.

Figure 10:
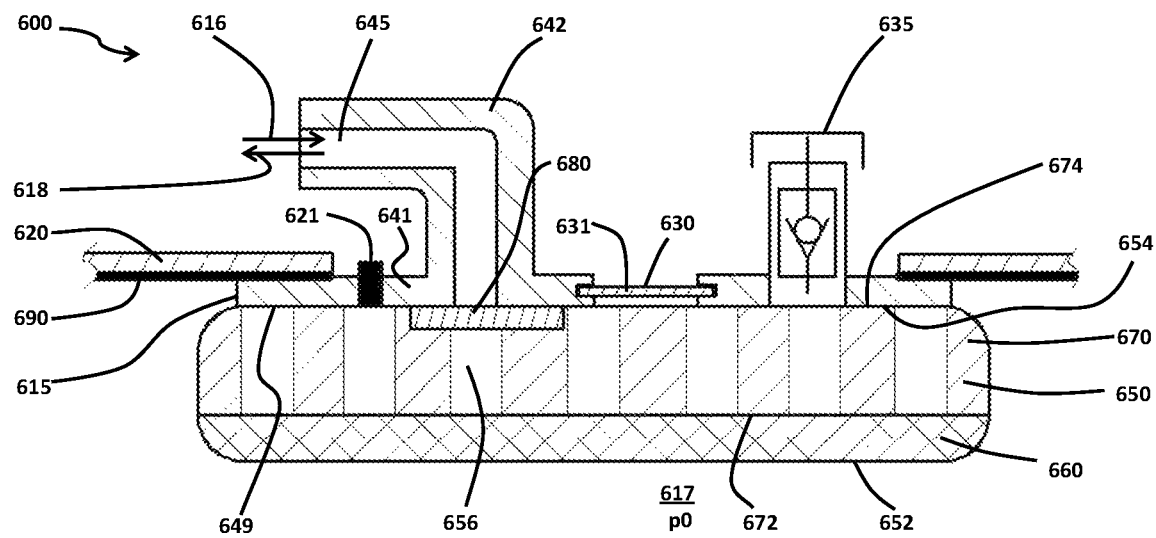
FIG. 10 illustrates by cross-sectional view portions of a seventh exemplary implementation of a wound therapy apparatus.

FIG. 10 illustrates portions of exemplary wound therapy apparatus 600. As illustrated in FIG. 10, wound therapy apparatus 600 includes wound interface 615. Wound interface 615, as illustrated, includes member 620 with adhesive layer 690 disposed thereon. Dressing 650 is secured to flange 641 of port 642 to fluidly communicate with lumen 645, as illustrated. Port 642 is secured to member 620 by portions of flange 641, and member 620 defines, at least in part, enclosed space 617 when wound interface 615 is secured to the skin surface by adhesive layer 690. Injection port 630 and pressure relief valve 635, which is symbolically represented, are disposed about flange 641, as illustrated. Injection port 630 or pressure relief valve 635 may have other dispositions about wound interface 615, in other implementations. Injection port 630 may be any of a variety of ports known in medical devices including, for example, Luer, compression-fit or self-sealing membrane types to allow introduction of medicament to dressing 650 or into enclosed space 617.

Injection port 630 includes membrane 631, in this implementation, and a needle cannula, for example, may be inserted through membrane 631 to supply a medicament therethrough to dressing 650 or generally within enclosed space 617. Membrane 631 may be formed of a self-sealable rubber or other such materials, and injection port 630 may be configured in ways that facilitate insertion of the hypodermic needle and supply of the medicament to dressing 650.

Pressure relief valve 635 is configured to allow the escape of fluid from enclosed space 517 when pressure $p_o$ within enclosed space 617 exceeds some limiting pressure $p_l$. The limiting pressure $p_l$ may be a pressure that, if exceeded, would cause structure 600 to become loosened from the skin surface.

Proximal side 654 of dressing 650 is engaged at least in part with distal side 649 of flange 641 as illustrated, and distal side 652 of dressing 650 is faced toward the wound bed. Dressing 650 includes distal layers 660 and proximal layer 670, as illustrated. Channels, such as channel 656, may optionally be formed in proximal layer 670 to convey input fluid 616 or output fluid 618 between distal side 672 and proximal side 674 of proximal layer 670, as illustrated. While channel 656 is illustrated as straight, it should be recognized that channel 656 may extend tortuously, and may have various extensions between distal side 672 and proximal side 674 of proximal layer 670.

Filter 680 may be interposed between proximal side 654 of dressing 650 and lumen 645 to remove exudate or other liquid but not gas from output fluid 618 as output fluid 618 passes from proximal side 654 of dressing 650 into lumen 645, as illustrated in FIG. 10. Filter 680 may also be interposed at any point between the dressing and the suction source, such as in the form of a disc filter or intra-lumen filter plug in the tubing, in order to prevent liquid from reaching the suction source. Removal of exudate or other liquid by filter 680 may prevent damage to components downstream of filter 680, such as pump 89 of controller 80 in wound therapy apparatus 10. Filter 680 may be formed of a variety of materials including polytetrafluoroethylene (PTFE).

As illustrated in FIGS. 8A, 8B, and 10, connectors 321, 323, connectors 421, 423, and connector 621 are disposed on one or more flanges, such as flange 641, for electrical communication with wound interfaces 315, 415, 615, respectively. Connectors 321, 323, 421, 423 621 are electrically conductive, in various implementations, for electrical communication with wound interface 315, 415, 615, of wound therapy apparatus 300, 400, 600, respectively, as illustrated. Portions of wound interface 315, 415, 615 including at least portions of dressing 350, 450, 650, respectively, may be formed of electrically conductive material. For example, portions of wound interface 615 including proximal layer 670 or distal layer 660 of dressing 650 may include electrically conductive material in electrical communication with connector 621.

Connectors 321, 421, connectors 323, 423 or connector 621 may be in electrical or electromagnetic communication by either wired or wireless pathways with a power source that flows power onto connectors 321, 421, 621, 323, 423 to create an electrical, magnetic, or electromagnetic field across at least a portion of the wound bed. In some implementations, a voltage gradient may be created between electrically conductive portions of wound interfaces 315, 415, 615 and a wound bed, while, in other implementations, electricity may be communicated through electrical pathways of wound interfaces 315, 415, 615 between connectors 321, 421 and connectors 323, 423, respectively, to create a magnetic field about the wound bed. Such electrical fields or magnetic fields may accelerate wound healing by increasing angiogenesis or stimulating immune response by increasing phagocytosis in macrophages.

Figure 11:
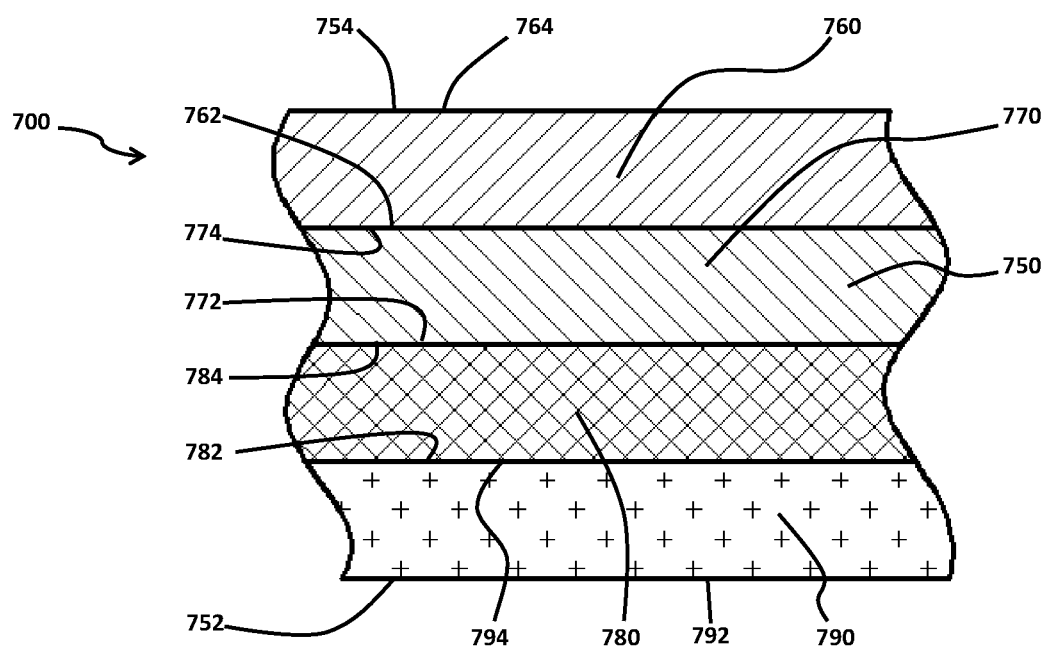
FIG. 11 illustrates by cross-sectional view portions of an eighth exemplary implementation of a wound therapy apparatus.

FIG. 11 illustrates portions of exemplary wound therapy apparatus 700 including dressing 750. In this implementation, dressing 750 has distal side 752 and proximal side 754. As illustrated in FIG. 11, dressing 750 includes proximal layer 760, first intermediary layer 770, second intermediary layer 780, and distal layer 790. Distal side 792 of distal layer 790 forms distal side 752 of dressing 750 that may bias against a wound bed, and proximal side 764 of proximal layer 760 forms proximal side 754 of dressing 750, as illustrated. Second intermediary layer 780, first intermediary layer 770, and proximal layer 760 are successively proximal of layer 790, as illustrated. Distal side 782 of second intermediary layer 780 is in biased engagement with proximal side 794 of distal layer 790, distal side 772 of first intermediary layer 770 is in biased engagement with proximal side 784 of second intermediary layer 780, and distal side 762 of proximal layer 760 is in biased engagement with proximal side 774 of first intermediary layer 770, in this exemplary implementation. Any or all of proximal layer 760, first intermediary layer 770, second intermediary layer 780, and distal layer 790 may be, for example, impregnated with various medicament(s) for delivery to the wound bed. Proximal layer 760, first intermediary layer 770, second intermediary layer 780, and distal layer 790 may be configured to confer various fluid related properties or to confer various mechanical properties, biological properties, or electrical properties onto dressing 750, in this implementation. Other implementations may have increasing numbers of intermediary layers, such as first intermediary layer 670 and second intermediary layer 780, for example, to include a third intermediary layer, fourth intermediary layer, or more.

Figure 12A:
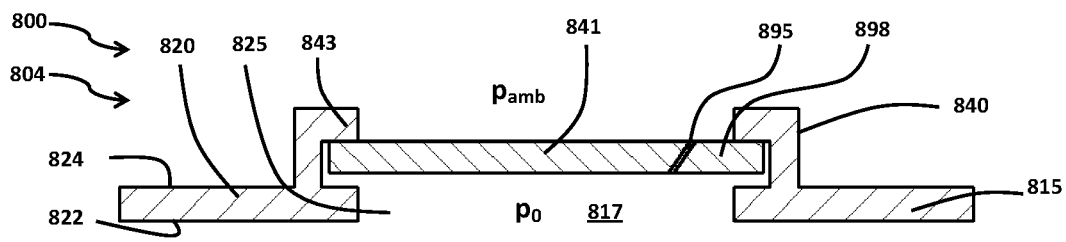
FIG. 12A illustrates by cross-sectional view portions of a ninth exemplary implementation of a wound therapy apparatus in a first stage of operation.
Figure 12B:
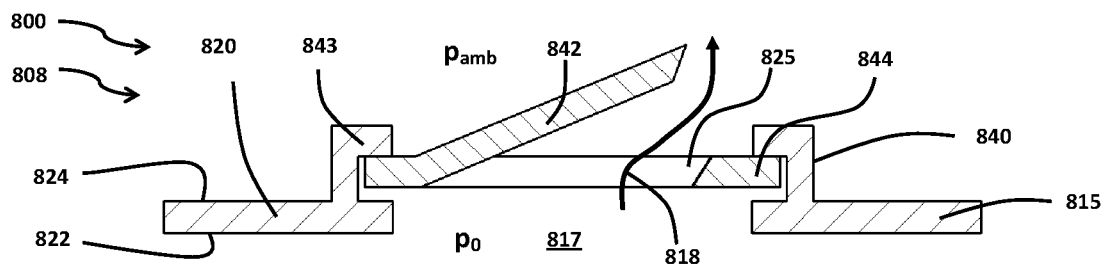
FIG. 12B illustrates by cross-sectional view portions of the exemplary wound therapy apparatus of FIG. 12A in a second stage of operation.

FIGS. 12A and 12B illustrate portions of wound therapy apparatus 800 including portions of wound interface 815. As illustrated, wound interface 815 includes member 820 and member 820 includes pressure relief valve 840. Pressure relief valve 840 is illustrated at first stage of operation 804 in FIG. 12A and at second stage of operation 808 in FIG. 12B. Member 820 of wound interface 815, at least in part, defines enclosed space 817 that is fluid-tight, in this implementation when wound interface 815 is secured to a skin surface. As illustrated in FIG. 12B, pressure relief valve 840 allows fluid 818 to escape from enclosed space 817 to reduce pressure $p_O$ when pressure $p_O$ within enclosed space 817 exceeds the ambient pressure $p_{amb}$ by a limiting pressure $p_l$ (i.e., $p_O - p_{amb} > p_l$). As illustrated, pressure relief valve 840 defines orifice 825 that passes between distal side 822 and proximal side 824 of member 820, as illustrated. Bracket 843 is disposed around the circumference of orifice 825, as illustrated. At first stage of operation 804, plate 841 is engaged with bracket 843 to seal orifice 825. Slot 895 formed in plate 841 provides a structural weakness in plate 841, and slot 895 is designed to cause plate 841 to deform structurally along slot 895 when pressure $p_O$ within enclosed space 817 exceeds limiting pressure $p_l$. When plate 841 deforms along slot 895, plate 841 bifurcates into plate sections 842, 844 allowing fluid 818 to escape from enclosed space 817 through orifice 825 thereby decreasing the pressure $p_O$ toward $p_{amb}$, in second stage of operation 808, as illustrated in FIG. 12B. Orifice 825 and plate 841 are illustrated as circular, but orifice 825, plate 841 and plate sections 842, 844 may have other geometric shapes, in other implementations.

Figure 13A:
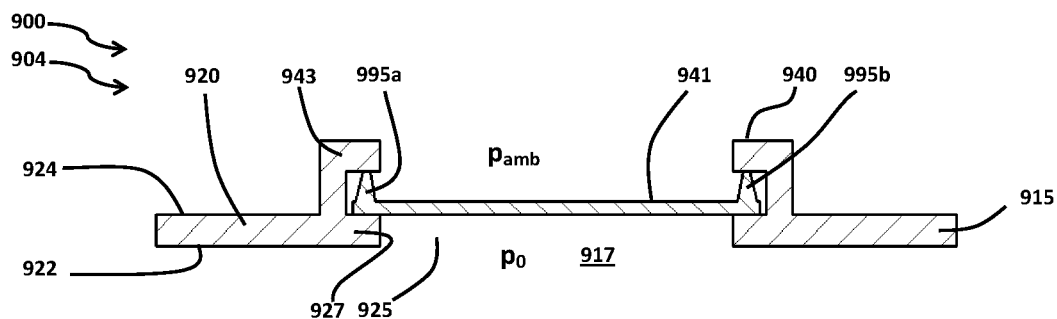
FIG. 13A illustrates by cross-sectional view portions of a tenth exemplary implementation of a wound therapy apparatus in a first stage of operation.
Figure 13B:
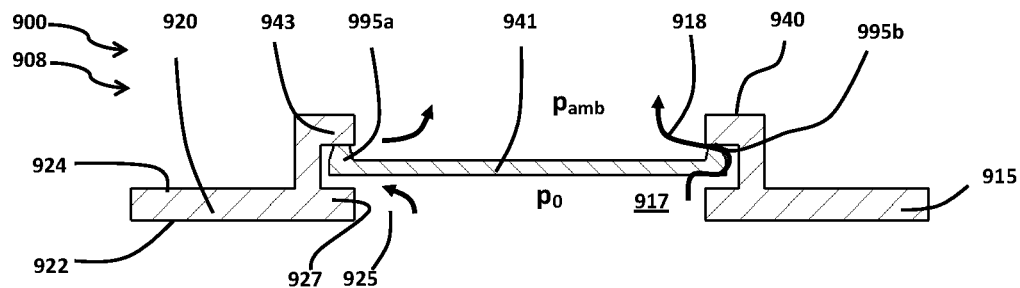
FIG. 13B illustrates by cross-sectional view portions of the exemplary wound therapy apparatus of FIG. 13A in a second stage of operation.
Figure 13C:
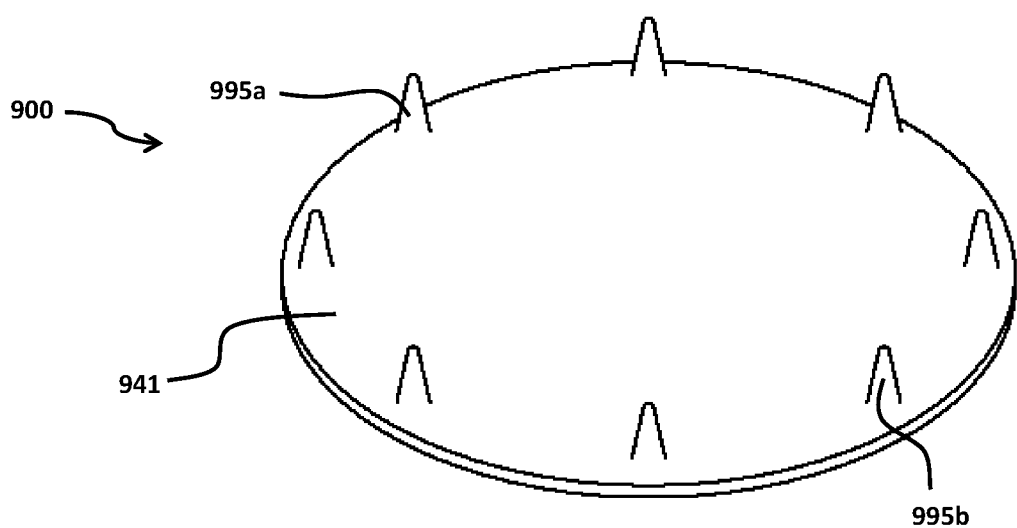
FIG. 13C illustrates by perspective view portions of the exemplary wound therapy apparatus of FIG. 13A; and, FIG. 14 illustrates by process flow chart an exemplary operational method of a wound therapy apparatus, such as the exemplary wound therapy apparatus of FIGS. 1A, 5, 7, 8A, 8B, 9, 10, 11, 12A, 13A.

FIGS. 13A, 13B, 13C illustrate portions of wound therapy apparatus 900 including portions of wound interface 915. Wound interface 915 includes member 920 and member 920 includes pressure relief valve 940, as illustrated. Member 920 of wound interface 915, at least in part, defines enclosed space 917 that is fluid-tight when wound interface 915 is secured to a skin surface, in this implementation. As illustrated, pressure relieve valve 940 allows fluid 918 to escape from enclosed space 917 to reduce pressure $p_O$ when pressure $p_O$ within enclosed space 917 exceeds the ambient pressure $p_{amb}$ by a limiting pressure $p_l$ (i.e., $p_O - p_{amb} > p_l$). Pressure relief valve 940 defines orifice 925 that passes between distal side 922 and proximal side 924 of member 920, as illustrated.

Pressure relief valve 940 is illustrated at first stage of operation 904 and second stage of operation 908 in FIGS. 13A and 13B, respectively. At first stage of operation 904, projections, such as projections 995a, 995b, disposed about plate 941 are engaged with bracket 943 that is disposed around the circumference of orifice 925 to force plate 941 into sealing engagement with flange 927, as illustrated in FIG. 13A. When pressure $p_O$ within enclosed space 917 exceeds the ambient pressure $p_{amb}$ by limiting pressure $p_l$, the projections, such as projections 995a, 995b, deform elastically to release plate 941 from sealing engagement with flange 927 thereby allowing fluid 918 to escape from enclosed space 917 through orifice 925 around the circumference of plate 941 between plate 941 and flange 927, which decreases the pressure $p_O$ toward $p_{amb}$, in second stage of operation 908, as illustrated in FIG. 13B. FIG. 13C illustrates projections, such as projections 995a, 995b, disposed circumferentially around plate 941. The projections, such as projections s 995a, 995b, are conic in shape in this implementation, but may assume other shapes, such as a circumferential ridge, in other implementations. Orifice 925, flange 927, bracket 943, and plate 941 are illustrated as circular, but may have other geometric shapes in other implementations.

In operation, a wound interface, such as wound interface 15, 115, 215, 225, 315, 415, 515, 615, 815, 915, of a wound therapy apparatus, such as wound therapy apparatus 10, 100, 200, 300, 400, 500, 600, 700, 800, 900 may be secured to a skin surface, such as skin surface 11, 111, 211, 311, 411, 511 around a wound bed, such as wound bed 13, 113, 513, to form an enclosed space, such as enclosed space 17, 117, 217, 227, 317, 417, 517, 617, 817, 917 over the wound bed. The enclosed space may be fluid-tight, and input fluid, such as input fluid 16, 116, 216, 316, 416, 616, may be input into the enclosed space or output fluid, such as output fluid 18, 118, 218, 318, 418, 618, may be withdrawn from the enclosed space through lumen, such as lumen 45, 47, 145, 245, 247, 345, 347, 445, 447, 645, defined by ports, such as ports 42, 44, 142, 242, 244, 342, 344, 442, 444, 642, disposed about the wound interface, by a controller, such as controller 80 of wound therapy apparatus 10.

Methods of operation may include biasing a dressing disposed within the enclosed space, such as dressing 50, 150, 250, 260, 350, 450, 550, 650, 750 against the wound bed. The dressing may include at least a distal layer, such as distal layer 60, 180, 580, 660, 790, and a proximal layer, such as proximal layer 70, 160, 570, 670, 760, and the dressing may be in fluid communication with one or more lumen that communicate input fluid into the dressing and that withdraw output fluid from the dressing. The dressing may fluidly communicate between the wound bed and the lumen thereby communicating input fluid input into the enclosed space through the lumen to the wound bed and communicating output fluid that may include exudate from the wound bed to the lumen for withdrawal from the enclosed space through the lumen. In some methods of operation, the distal layer and the proximal layer may be formed of materials cooperating in communicating exudate from the wound bed to the lumen for withdrawal from the enclosed space. In some methods of operation, the dressing may include intermediary layers, such as intermediary layer 170, first intermediary layer 670, and second intermediary layer 680, that deliver a medicament, such as medicament 177, to the wound bed. The intermediary layers may be impregnated with the medicament at least during portions of the usage of the wound therapy apparatus. In some methods of operation, the distal layer or the proximal layer may be impregnated with a medicament, and the medicament may be delivered from the distal layer or proximal layer, respectively, to the wound bed. In some methods of operation, the dressing may be impregnated with an agent that, for example, prevents bacterial growth within the dressing. Some methods of operation may include biasing a distal layer formed of perforated silicone against the wound bed to promote healing with minimal or no scarring resulting from surgical incisions.

In operation, input fluid may be input into the enclosed space or output fluid may be withdrawn from the enclosed space through one or more lumen to vary the pressure $p_0$ within the enclosed space over a pressure range $p_{min} \leq p_0 \leq p_{max}$. For example, output fluid may be withdrawn from the enclosed space to reduce pressure $p_0$ to minimum pressure $p_{min}$ where $p_{min}$ is less than the ambient pressure $p_{amb}$. The pressure $p_0$ may be maintained at $p_{min} < p_{amb}$ (suction or negative pressure) for some period of time during which output fluid including exudate, such as exudate 19, 119, is withdrawn from the enclosed space. The pressure $p_0$ may then be increased to a maximum pressure $p_{max}$ by input of input fluid into the enclosed space. The input fluid may be a gas, such as gas 83, and the gas may have an $O_2$ concentration greater than that of atmospheric air, so that the $O_2$ concentration within the enclosed space is greater than that of atmospheric air and the wound bed is exposed to enhanced concentrations of $O_2$. Following the input of input fluid with $O_2$ concentration greater than that of atmospheric air, output fluid may be withdrawn from the enclosed space to reduce the pressure $p_0$ to minimum pressure $p_{min}$. Whenever the suction is relieved by input fluid with enriched oxygen, the wound bed is exposed to enhanced concentrations of $O_2$ at pressure $p_0$ equal to minimum pressure $p_{min}$. The wound bed thus receives the benefits of exposure to enhanced concentration of $O_2$ along with the benefits of suction therapy.

In some exemplary operations, the input fluid may be liquid, such as liquid 85, and the input of liquid may increase the pressure $p_0$ to the maximum pressure $p_{max}$. The liquid may provide therapeutic benefit to the wound bed, to the skin surface surrounding the wound bed, or to both the wound bed and the skin surface surrounding the wound bed.

Methods of operation may include the application of cycles of suction ($p_o < p_{amb}$) to the wound bed wherein at least one suction cycle is relieved by input of input fluid having concentration of $O_2$ greater then that of atmospheric air.

Figure 14:
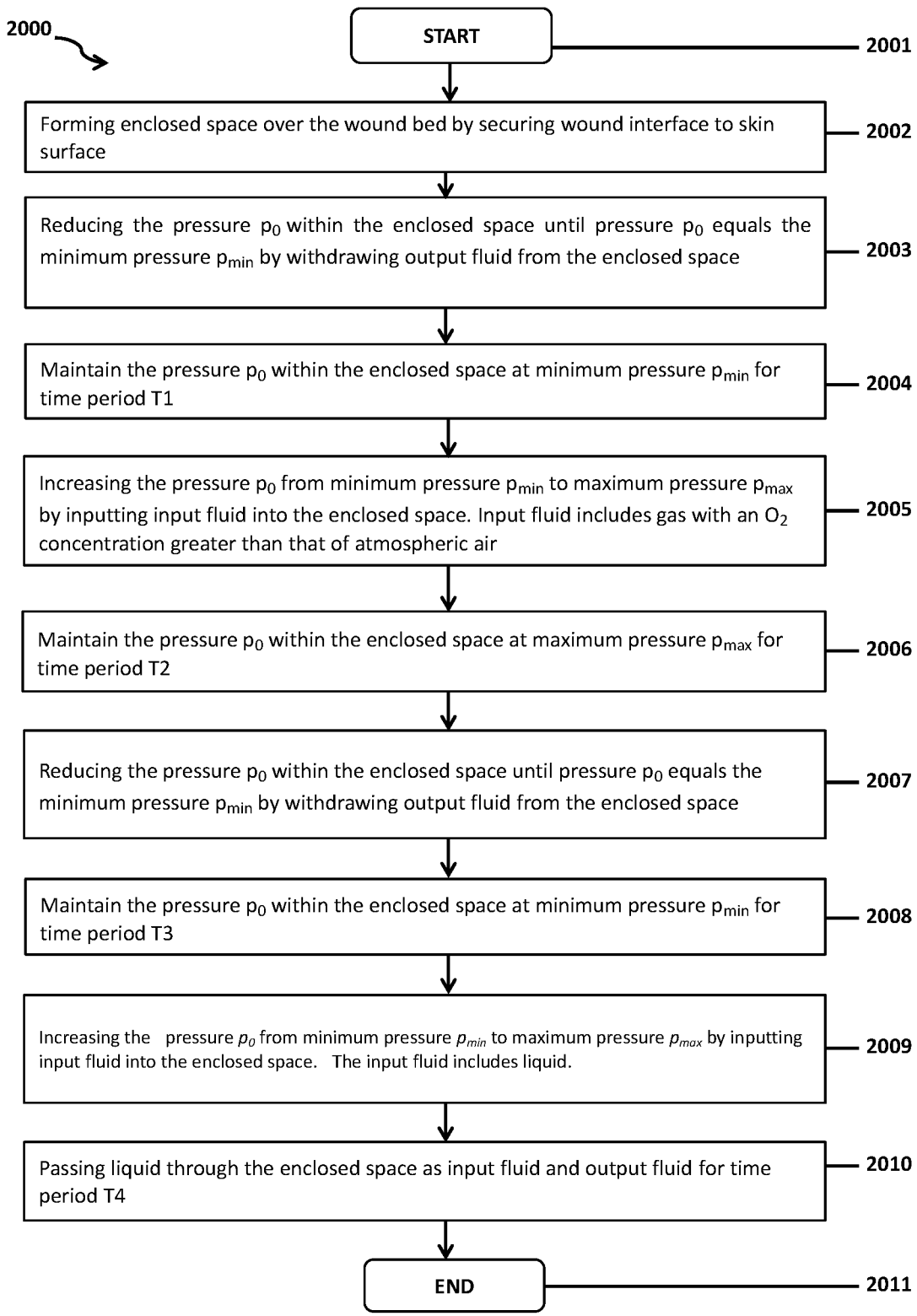

These operations are generally illustrated by operational method 2000, as illustrated by process flow chart in FIG. 14. Operational method 2000 as illustrated in FIG. 14 and the associated description is exemplary only. As illustrated in FIG. 14, operational method 2000 is entered at step 2001. At step 2002, the wound interface of the wound therapy apparatus is secured to the skin surface forming the enclosed space over the wound bed. At step 2003, output fluid is withdrawn from the enclosed space thereby reducing the pressure $p_0$ within the enclosed space until $p_0$ equals the minimum pressure $p_{min}$. Pressure $p_0$ within the enclosed space may then be maintained at minimum pressure $p_{min}$ for time period $T_1$, as per step 2004. For example, time period $T_1$ may be about 3 to 5 minutes. At step 2005, input fluid is input into the enclosed space thereby increasing the pressure $p_0$ from minimum pressure $p_{min}$ to maximum pressure $p_{max}$. The input fluid input into the enclosed space at exemplary step 2005 to increase the pressure $p_0$ from minimum pressure $p_{min}$ to maximum pressure $p_{max}$ comprises a gas with an $O_2$ concentration greater than that of atmospheric air.

At step 2006, the maximum pressure $p_{max}$ may be about ambient pressure $p_{amb}$, maximum pressure $p_{max}$ may be greater than ambient pressure $p_{amb}$, or maximum pressure $p_{max}$ may be less than ambient pressure $p_{amb}$, in various implementations. Pressure $p_0$ within the enclosed space may then be maintained at maximum pressure $p_{max}$ for time period $T_2$, as per exemplary step 2006. For example, time period $T_2$ may be about 1-3 minutes.

As illustrated in FIG. 14, output fluid is withdrawn from the enclosed space at step 2007 to reduce the pressure $p_0$ within the enclosed space until $p_0$ equals the minimum pressure $p_{min}$. Pressure $p_0$ within the enclosed space may then be maintained at minimum pressure $p_{min}$ for time period $T_3$, as per step 2008. Because the fluid input into the enclosed space at step 2005 comprises a gas with an $O_2$ concentration greater than that of atmospheric air, the wound bed is exposed to gas with an $O_2$ concentration greater than that of atmospheric air throughout steps 2006, 2007, and 2008, in exemplary operational method 2000.

At step 2009, input fluid is input into the enclosed space to increase the pressure $p_0$ from minimum pressure $p_{min}$ to maximum pressure $p_{max}$. The input fluid at step 2009 comprises a liquid, in exemplary operational method 2000.

Output fluid is withdrawn from the enclosed space and input fluid is input into the enclosed space sequentially in performing steps 2003, 2004, 2005, 2006, 2007, 2008 and 2009, in exemplary operational method 2000, so that either input fluid is being input or output fluid is being withdrawn. Input fluid is not input at the same time output fluid is being withdrawn in performing steps 2003, 2004, 2005, 2006, 2007, 2008 and 2009 of exemplary operational method 2000.

At step 2010, liquid is then passed through the enclosed space for time period $T_4$. The liquid may be sequentially input into the enclosed space and then withdrawn from the enclosed space or the liquid may be simultaneously input into the enclosed space and withdrawn from the enclosed space, at step 2010. Liquid may be input in pulses to purge blockages within various passages that fluidly communicate with the enclosed space, at step 2010. At step 2010, the liquid may flush out the enclosed space including the wound bed and dressing, remove bioburden or exudate, cleanse the wound bed, hydrate the wound bed, for example. At step 2010, the liquid may be input and withdrawn by instillation (steady flow). Exemplary operational method 2000 then terminates at step 2011.

Liquid may be input into the enclosed space at step 2010 by being sucked in from a source, such as source 84, by pressure $p_0$ within the enclosed space less than ambient pressure $p_{amb}$. As liquid fills the enclosed space, the pressure $p_0$ may tend toward ambient pressure $p_{amb}$ reaching ambient pressure $p_{amb}$ when the enclosed space is filled by liquid. In certain implementations, there is no energy gradient between the liquid source and the enclosed space other than pressure difference $p_{amb}-p_0$ so that liquid flow into the enclosed space ceases once $p_0=p_{amb}$ thus preventing overfilling of the enclosed space that may dislodge the wound interface. In other implementations, the controller may limit the pressure $p_0$ of the liquid within the enclosed space for example to about ambient pressure $p_{amb}$ in order to prevent dislodgement of the wound interface.

Exemplary method 2000 may be repeated any number of times with various combinations of steps 2003, 2004, 2005, 2006, 2007, 2008, 2009, 2010. Note that minimum pressure $p_{min}$ and maximum pressure $p_{max}$ may differ in steps 2003, 2004, 2005, 2006, 2007, 2008, 2009, 2010, and times $T_1, T_2, T_3, T_4$ as well as minimum pressure $p_{min}$ and maximum pressure $p_{max}$ may be altered during various repetitions of method 2000.

Some operational methods may include the step of supplying medicament to the dressing while the dressing is engaged with the wound bed, and the medicament may be supplied, for example, through the lumen or through an injection port, such as injection port 630, provided for that purpose.

In some methods of operation, a pressure relief valve, such as pressure relief valve 635, 840, 940, may operate to reduce the pressure $p_0$ within the enclosed space to no more than a desired liming pressure $p_l$ when the pressure $p_0$ within the enclosed space exceeds limiting pressure $p_l$ above the ambient pressure $p_{amb}$.

The foregoing discussion along with the Figures discloses and describes various exemplary implementations. These implementations are not meant to limit the scope of coverage, but, instead, to assist in understanding the context of the language used in this specification and in the claims. The Abstract is presented to meet requirements of 37 C.F.R. § 1.72(b) only, and is not intended to identify key elements of apparatus, methods, and compositions of matter disclosed herein or to delineate the scope thereof. Upon study of this disclosure and the exemplary implementations herein, one of ordinary skill in the art may readily recognize that various changes, modifications and variations can be made thereto without departing from the spirit and scope of the inventions as defined in the following claims.

The invention claimed is:

1. A wound therapy apparatus, comprising:
   a wound interface adapted to be secured to a skin surface around a wound bed to form an enclosed space over the wound bed that is fluid-tight;
   a dressing engaged with the wound interface within the enclosed space;
   connectors disposed upon the wound interface for electrical communication with the wound interface to generate an electromagnetic field about the wound bed;
   a lumen passing through the wound interface for fluid communication with the enclosed space; and
   gas having an $O_2$ concentration greater than that of atmospheric air, the gas is sequentially input into the enclosed space and withdrawn from the enclosed space via the lumen to vary a pressure $p_0$ within the enclosed space over a pressure cycle having pressure range $p_{min} \leq p_0 \leq p_{max}$ where $p_{min}$ is a minimum pressure during the pressure cycle and $p_{max}$ is a maximum pressure during the pressure cycle.

2. The apparatus of claim 1, wherein the dressing comprises a distal layer comprised of silicone, and a distal side of the distal layer is adapted to contact the wound bed.

3. The apparatus of claim 1, further comprising:
   a second lumen passing through the wound interface for fluid communication with the enclosed space.

4. The apparatus of claim 1, wherein the maximum pressure $p_{max}$ is within the range of from −15 mm Hg to +40 mm Hg with respect to ambient pressure $p_{amb}$.

5. The apparatus of claim 1, wherein the minimum pressure $p_{min}$ is within the range of from −40 mm Hg to −150 mm with respect to ambient pressure $p_{amb}$.

6. The apparatus of claim 1, wherein the dressing comprises medicament for delivery to the wound bed.

7. The apparatus of claim 1, further comprising:
   a port that cooperates with the wound interface to deliver medicament into the enclosed space.

8. A wound therapy apparatus, comprising:
   a wound interface securable to a skin surface around a wound bed to form an enclosed space over the wound bed that is fluid-tight;
   a dressing engaged with the wound interface within the enclosed space;
   a lumen passing through the wound interface that fluidly communicates with the enclosed space;
   a filter disposed between the dressing and a suction source to limit flow of exudate towards the suction source, the suction source providing suction to the lumen; and
   gas having an $O_2$ concentration greater than that of atmospheric air, the gas is sequentially input into the enclosed space and withdrawn from the enclosed space via the lumen to vary the pressure $p_0$ within the enclosed space over a pressure cycle having pressure range $p_{min} \leq p_0 \leq p_{max}$ where $p_{min}$ is a minimum pressure during the pressure cycle and $p_{max}$ is a maximum pressure during the pressure cycle.

9. A wound therapy apparatus, comprising:
   a wound interface securable to a skin surface around a wound bed to form an enclosed space over the wound bed that is fluid-tight;

a pressure $p_0$ within the enclosed space that differs from the ambient pressure $p_{amb}$, the pressure $p_0$ being in the range of from −150 mm Hg to +40 mm Hg with respect to ambient pressure $p_{amb}$;

a port disposed about the wound interface with a lumen passing through the port that fluidly communicates with the enclosed space;

a dressing engaged with the wound interface within the enclosed space, the dressing comprising a distal layer comprised, at least in part, of silicone, a distal side of the distal layer adapted to contact the wound bed;

a spacer disposed within the enclosed space between the dressing and the lumen to define a plenum in fluid communication with the lumen and with a proximal side of the dressing; and fenestrations disposed in the distal layer that fluidly communicate between the distal side and a proximal side of the distal layer.

10. The apparatus of claim 9, further comprising:
gas within the enclosed space having an $O_2$ concentration greater than the $O_2$ concentration of atmospheric air.

11. A wound therapy apparatus, comprising:
a wound interface securable to a skin surface around a wound bed to form an enclosed space over the wound bed that is fluid-tight;

a pressure $p_0$ within the enclosed space differing from the ambient pressure $p_{amb}$, the pressure $p_0$ being in the range of from −150 mm Hg to +40 mm Hg with respect to ambient pressure $p_{amb}$;

a dressing engaged with the wound interface within the enclosed space, the dressing comprising a distal layer comprised, at least in part, of silicone, a distal side of the distal layer adapted to contact the wound bed;

a hydrophobic material in fluid cooperation with a proximal side of the distal layer to transfer exudate away from the proximal side of the distal layer;

a hydrophilic material in fluid cooperation with the hydrophobic material to transfer exudate away from the hydrophobic material; and fenestrations disposed in the distal layer that fluidly communicate between the distal side and the proximal side of the distal layer.

12. The apparatus of claim 11, further comprising:
gas within the enclosed space having an $O_2$ concentration greater than the $O_2$ concentration of atmospheric air.

13. The apparatus of claim 11, further comprising:
a port disposed about the wound interface with a lumen passing through the port that fluidly communicates with the enclosed space.

14. A wound therapy apparatus, comprising:
a wound interface securable to a skin surface around a wound bed to form an enclosed space over the wound bed that is fluid-tight in order that a pressure $p_0$ within the enclosed space differs from ambient pressure $p_{amb}$, the pressure $p_0$ being in the range of from −150 mm Hg to +40 mm Hg with respect to ambient pressure $p_{amb}$;

a dressing engaged with the wound interface to contact the wound bed;

gas within the enclosed space having an $O_2$ concentration greater than atmospheric air; and a hydrophobic material that forms a portion of the dressing, the hydrophobic material transferring exudate from the wound bed; and a hydrophilic material in fluid cooperation with the hydrophobic material to transfer exudate from the hydrophobic material.

15. The apparatus of claim 14, further comprising:
one or more connectors disposed upon the wound interface for electrical communication with the wound interface to generate an electromagnetic field about the wound bed.

16. The apparatus of claim 14, wherein the dressing comprises a distal layer comprised of silicone, and a distal side of the distal layer contacts the wound bed.

17. The apparatus of claim 14, further comprising:
a port disposed about the wound interface with a lumen passing through the port that fluidly communicates with the enclosed space.

18. The apparatus of claim 14, wherein the pressure $p_0$ within the enclosed space is varied over a pressure cycle having pressure range $p_{min} \leq p_0 \leq p_{max}$ where $p_{min}$ is a minimum pressure during the pressure cycle and $p_{max}$ is a maximum pressure during the pressure cycle.

19. The apparatus of claim 18, wherein the maximum pressure $p_{max}$ is within the range of from 15 mm Hg to +40 mm Hg with respect to ambient pressure $p_{amb}$.

20. The apparatus of claim 18, wherein the minimum pressure $p_{min}$ is within the range of from −40 mm Hg to −150 mm with respect to ambient pressure $p_{amb}$.

* * * * *